US012637431B2

(12) United States Patent
Rajan et al.

(10) Patent No.: US 12,637,431 B2
(45) Date of Patent: May 26, 2026

(54) PROCESS FOR THE PREPARATION OF 5-[[[(2S)-2-AMINO-3-[4-(AMINOCARBONYL)-2,6-DIMETHYLPHENYL]-1-OXOPROPYL][(1S)-1-(4-PHENYL-1H-IMIDAZOL-2-YL)ETHYL]AMINO]METHYL-2-METHOXYBENZOIC ACID AND ITS POLYMORPHS THEREOF

(71) Applicant: MSN LABORATORIES PRIVATE LIMITED, Hyderabad (IN)

(72) Inventors: Srinivasan Thirumalai Rajan, Hyderabad (IN); Eswaraiah Sajja, Hyderabad (IN); Rajeshwar Reddy Sagyam, Hyderabad (IN); Prabhakar Macharla, Hyderabad (IN); Rajesham Boge, Hyderabad (IN)

(73) Assignee: MSN Laboratories Private Limited, R&D Center, Hyderabad (IN)

( * ) Notice: Subject to any disclaimer, the term of this patent is extended or adjusted under 35 U.S.C. 154(b) by 223 days.

(21) Appl. No.: 16/099,141

(22) PCT Filed: May 2, 2017

(86) PCT No.: PCT/IN2017/000098

§ 371 (c)(1),
(2) Date: Dec. 9, 2019

(87) PCT Pub. No.: WO2017/191650

PCT Pub. Date: Nov. 9, 2017

(65) Prior Publication Data

US 2019/0177281 A1 Jun. 13, 2019

(30) Foreign Application Priority Data

| | | |
|---|---|---|
| May 3, 2016 | (IN) | 201641015345 |
| Jul. 6, 2016 | (IN) | 201641023195 |
| Jan. 23, 2017 | (IN) | 201741002480 |
| Jan. 23, 2017 | (IN) | 201741002481 |

(51) Int. Cl.
*C07D 233/64* (2006.01)
*C07C 31/12* (2006.01)

(52) U.S. Cl.
CPC ............ *C07D 233/64* (2013.01); *C07C 31/12* (2013.01); *C07B 2200/13* (2013.01)

(58) Field of Classification Search
CPC .......................... C07D 233/64; C07B 2200/13
See application file for complete search history.

(56) References Cited

FOREIGN PATENT DOCUMENTS

WO WO 2017/153471 * 9/2017 ................ A61P 1/06

* cited by examiner

*Primary Examiner* — Alicia L Otton
(74) *Attorney, Agent, or Firm* — Parithosh K. Tungaturthi

(57) ABSTRACT

The present invention relates to an improved process for the preparation of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1, and polymorphs thereof, the compound of formula-1 is further represented by the following structural formula:

Formula-1

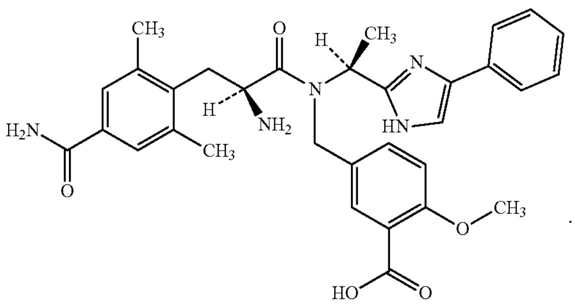

.

5 Claims, 9 Drawing Sheets

PROCESS FOR THE PREPARATION OF 5-[[[(2S)-2-AMINO-3-[4-(AMINOCARBONYL)-2,6-DIMETHYLPHENYL]-1-OXOPROPYL][(1S)-1-(4-PHENYL-1H-IMIDAZOL-2-YL) ETHYL]AMINO] METHYL-2-METHOXYBENZOIC ACID AND ITS POLYMORPHS THEREOF

RELATED APPLICATIONS

This application is a national phase application under 35 U.S.C. § 371 of International Application Number PCT/IN2017/000098, filed on May 2, 2017, which claims priority to Indian Patent Application Numbers 201641015345 filed on May 3, 2016; 201641023195 filed on Jul. 6, 2016; 201741002480 filed on Jan. 23, 2017; and 201741002481 filed on Jan. 23, 2017; the disclosures of all of which are hereby incorporated by reference in their entirety.

FIELD OF THE INVENTION

The present invention relates to an improved process for the preparation of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1, represented by the following structural formula:

Formula-1

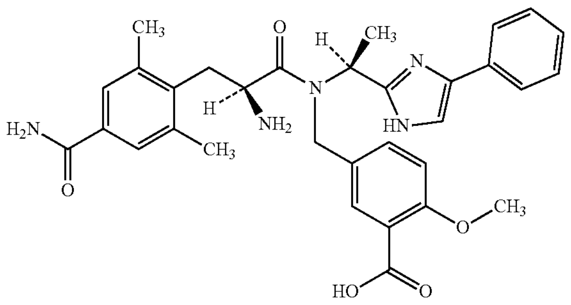

The present invention also relates to novel crystalline forms and amorphous solid dispersions of 5-[[[(2S)-2-amino-3-[4-(aminocarbonyl)-2,6-dimethylphenyl]-1-oxopropyl][(1S)-1-(4-phenyl-1H-imidazol-2-yl) ethyl]amino] methyl]-2-methoxybenzoic acid compound of formula-1.

Further, the present invention also relates to acid addition salts of (S)-methyl-2-methoxy-5-(((1-(4-phenyl-1H-imidazol-2-yl)ethyl)amino)methyl)benzoate compound of general formula-4.

BACKGROUND OF THE INVENTION

5-[[[(2S)-2-Amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid known as Eluxadoline and is approved by USFDA under the brand name VIBERZI for the treatment of irritable bowel syndrome with diarrhea. Irritable bowel syndrome is a long-term disorder of the gut with pain or discomfort in the abdomen (belly), bloating and altered bowel habit. European Commission granted a marketing authorization for Eluxadoline (Truberzi) on 19 Sep. 2016.

5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid and process for its preparation was first disclosed in U.S. Pat. No. 7,741,356 B2 herein after referred as US'356 B2.

U.S. Pat. No. 7,994,206 B2 discloses the process for the preparation of Eluxadoline by treating boc protected Eluxadoline with hydrochloric acid to provide Eluxadoline hydrochloride, which is further treated with sodium hydroxide to provide Eluxadoline with low yield and purity. The said process suffers from several drawbacks such as cumbersome workup, compound of formula-1 is obtained as gummy semi-solid which is difficult to isolate and requires tedious purifications and finally provide compound of formula-1 with low yield.

In view of the above drawbacks, there is an unmet need to develop cost-effective, environmental friendly and commercially viable process for the preparation of Eluxadoline compound of formula-1 with high yield and purity.

U.S. Pat. No. 8,691,860 B2 discloses crystalline form-α of 5-[[[(2S)-2-amino-3-[4-(amino carbonyl)-2,6-dimethylphenyl]-1-oxopropyl][(1S)-1-(4-phenyl-1H-imidazol-2yl) ethyl]amino] methyl]-2-methoxybenzoic acid compound of formula-1.

U.S. Pat. No. 7,994,206 B2 discloses crystalline form-β of 5-[[[(2S)-2-amino-3-[4-(amino carbonyl)-2,6-dimethylphenyl]-1-oxopropyl][(1S)-1-(4-phenyl-1H-imidazol-2yl)ethyl] amino]methyl]-2-methoxybenzoic acid compound of formula-1.

U.S. Pat. No. 8,609,865 B2 discloses process for the preparation of crystalline form-α and form-β of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino] methyl]-2-methoxybenzoic acid compound of formula-1.

IPCOM000245114D publication discloses crystalline forms of methyl 5-(((2S)-2-amino-3-(4-carbamoyl-2,6-dimethylphenyl)-N-((1S)-1-(4-phenyl-1H-imidazol-2-yl)ethyl) propanamido)methyl)-2-methoxybenzoate dihydrochloride.

The said US'356 B2 discloses hydrochloric acid salt of 5-[[[(2S)-2-amino-3-[4-(amino carbonyl)-2,6-dimethylphenyl]-1-oxopropyl][(1S)-1-(4-phenyl-1H-imidazol-2-yl) ethyl]amino]methyl]-2-methoxybenzoic acid compound of formula-1a but, does not have any information about the free base of compound of formula-1.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid state forms of a drug, including all polymorphic forms, and to determine the stability, dissolution and flow properties of each polymorphic form.

BRIEF DESCRIPTION OF THE INVENTION

The first aspect of the present invention is to provide an improved process for the preparation of amorphous form of 5-[[[(2S)-2-amino-3-[4-(aminocarbonyl)-2,6-dimethyl phenyl]-1-oxopropyl][(1S)-1-(4-phenyl-1H-imidazol-2yl)ethyl] amino]methyl]-2-methoxy benzoic acid compound of formula-1.

The second aspect of the present invention is to provide 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid 2-butanol solvate compound of formula-1 and process for its preparation.

The third aspect of the present invention is to provide a novel, accurate and sensitive HPLC method for analyzing 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1 and its intermediates.

The fourth aspect of the present invention is to provide crystalline form of 5-(((2S)-2-((tert-butoxycarbonyl)amino)-3-(4-carbamoyl-2,6-dimethylphenyl)-N-((1S)-1-(4-phenyl-1H-imidazol-2-yl)ethyl)propanamido)methyl)-2-methoxy benzoate lithium salt compound of formula-5b, herein after designated as form-S1 and process for its preparation.

The fifth aspect of the present invention is to provide 5-(((2S)-2-((tert-butoxy carbonyl)amino)-3-(4-carbamoyl-2,6-dimethylphenyl)-N-((1S)-1-(4-phenyl-1H-imidazol-2-yl)ethyl)propanamido)methyl)-2-methoxy benzoate sodium salt compound of formula-5a.

The sixth aspect of the present invention is to provide a process for the preparation of amorphous form of 5-[[[(2S)-2-amino-3-[4-(aminocarbonyl)-2,6-dimethylphenyl]-1-oxo propyl][(1S)-1-(4-phenyl-1H-imidazol-2yl)ethyl]amino]methyl]-2-methoxybenzoic acid compound of formula-1.

The seventh aspect of the present invention is to provide a novel crystalline form of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1 herein after designated as form-N and process for its preparation.

The eighth aspect of the present invention is to provide a novel crystalline form of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1 herein after designated as form-M1 and process for its preparation.

The ninth aspect of the present invention is to provide a novel crystalline form of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1 herein after designated as form-M2 and process for its preparation.

The tenth aspect of the present invention is to provide acid addition salts of (S)-methyl-2-methoxy-5-(((1-(4-phenyl-1H-imidazol-2-yl)ethyl)amino)methyl)benzoate compound of formula-2 and process for its preparation.

The eleventh aspect of the present invention is to provide the novel crystalline maleate salt of (S)-methyl-2-methoxy-5-(((1-(4-phenyl-1H-imidazol-2-yl)ethyl)amino)methyl) benzoate compound of formula-2a, herein after designated as form-M and process for its preparation.

The twelfth aspect of the present invention is to provide the novel crystalline oxalate salt of (S)-methyl-2-methoxy-5-(((1-(4-phenyl-1H-imidazol-2-yl)ethyl)amino)methyl) benzoate compound of formula-2b, herein after designated as form-S and process for its preparation.

The thirteenth aspect of the present invention relates to novel intermediate compound of formula-12, 13, 14, 15 which are useful in the preparation of compound of formula-1.

The fourteenth aspect of the present invention is to provide novel process for the preparation of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1.

The fifteenth aspect of the present invention is to provide an improved process for the preparation of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1.

The sixteenth aspect of the present invention is to provide novel crystalline form of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1, herein after designated as Form-N1 and its preparation thereof.

The seventeenth aspect of the present invention is to provide novel crystalline form of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1, herein after designated as Form-N2 and its preparation thereof.

The eighteenth aspect of the present invention is to provide novel crystalline form of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1, herein after designated as Form-N3 and its preparation thereof.

The nineteenth aspect of the present invention is to provide amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with one or more pharmaceutical acceptable carrier and process for their preparation.

BRIEF DESCRIPTION OF THE DRAWINGS

FIG. 3: Illustrates the PXRD pattern of crystalline form-S2 of 5-(((2S)-2-((tert-butoxy carbonyl)amino)-3-(4-carbamoyl-2,6-dimethylphenyl)-N-((1S)-1-(4-phenyl-1H-imidazol-2-yl)ethyl)propanamido)methyl)-2-methoxy benzoate sodium salt compound of formula-5a.

FIG. 8: Illustrates the PXRD pattern of crystalline form-M of maleate salt of (S)-methyl-2-methoxy-5-(((1-(4-phenyl-1H-imidazol-2-yl)ethyl)amino)methyl)benzoate compound of formula-2a.

FIG. 14: Illustrates the PXRD pattern of amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl) ethyl]amino]methyl]-2-methoxybenzoic acid in combination with HPMC AS.

DETAILED DESCRIPTION OF THE INVENTION

Figure 1:
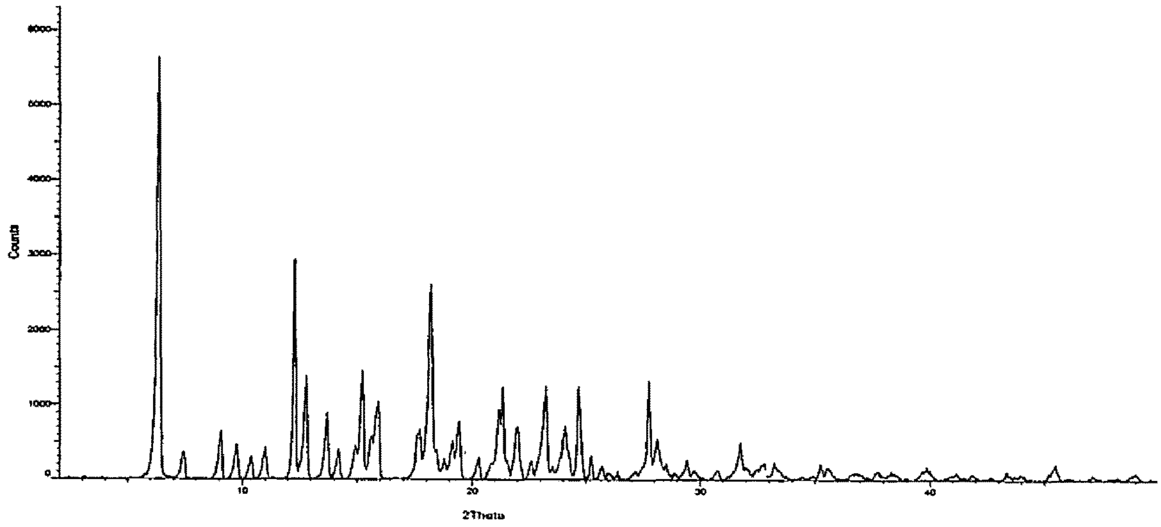
FIG. 1: Illustrates the PXRD pattern of crystalline form-M of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid 2-butanol solvate compound of formula-1.

As used herein the term "suitable solvent" used in the present invention refers to "hydrocarbon solvents" such as n-hexane, n-heptane, cyclohexane, pet ether, toluene, pentane, cycloheptane, methylcyclohexane, m-, o-, or p-xylene, and the like; "ether solvents" such as dimethoxy methane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, 1,2-dimethoxy ethane and the like; "ester solvents" such as methyl acetate, ethyl acetate, isopropyl acetate, n-butyl acetate and the like; "polar-aprotic solvents such as dimethylacetamide (DMA), dimethylformamide (DMF), dimethyl sulfoxide (DMSO), N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutylketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol, 2-nitroethanol, 2-fluoroethanol, 2,2,2-trifluoroethanol, ethylene glycol, propylene glycol, 2-methoxyethanol, 1,2-ethoxyethanol, diethylene glycol, 1, 2, or 3-pentanol, neo-pentyl alcohol, t-pentyl alcohol, diethylene glycol monoethyl ether, cyclohexanol, anisole, benzyl alcohol, phenol, or glycerol and the like; "polar solvents" such as water or mixtures thereof.

The term "suitable base" used herein the present invention until unless specified is selected from inorganic bases like "alkali metal hydroxides" such as lithium hydroxide, sodium hydroxide, potassium hydroxide and the like; "alkali metal carbonates" such as sodium carbonate, potassium carbonate, lithium carbonate and the like; "alkali metal bicarbonates" such as sodium bicarbonate, potassium bicarbonate, lithium bicarbonate and the like; "alkali metal hydrides" such as potassium hydride, lithium hydride and the like; "alkali metal alkoxides" such as sodium methoxide, sodium ethoxide, sodium tert-butoxide, potassium methoxide, potassium ethoxide, potassium tert-butoxide and the like; ammonia; and organic bases such as triethyl amine, methyl amine, ethyl amine, 1,8-diazabicyclo [5.4.0]undec-7-ene (DBU), 1,5-diazabicyclo (4.3.0)non-5-ene (DBN), lithium dioisopropyl amide (LDA), n-butyl lithium, tribenzylamine, isopropyl amine, diisopropyl amine, diisopropylethylamine, N-methylmorpholine, N-ethylmorpholine, piperidine, dimethyl aminopyridine, morpholine, pyridine, 2,6-lutidine, 2,4,6-collidine, imidazole, 1-methyl imidazole, 1,2,4-triazole, 1,4-diazabicyclo[2.2.2]octane (DABCO) or mixtures thereof.

The suitable hydrochloric acid source is selected from HCl gas, aqueous HCl, dry HCl, ethyl acetate-HCl, IPA-HCl, ethanol-HCl, methanol-HCl.

The "coupling agent" is selected from N,N'-dicyclohexylcarbodiimide (DCC), N,N'-diisopropylcarbodiimide (DIC), 1-ethyl-3-(3-dimethylaminopropyl) carbodiimide HCl (EDC.HCl), alkyl or aryl chloroformates such as ethylchloro formate, benzylchloroformate, diphenylphosphoroazidate (DPPA), (Benzotriazol-1-yloxy)tripyrrolidinophosphoniumhexa fluorophosphate, methanesulfonyl chloride and the like optionally in combination with 1-hydroxy-7-azatriazole (HOAt), 1-hydroxybenzotriazole (HOBt), 1-hydroxy-1H-1,2,3-triazole-4-carboxylate (HOCt), N-hydroxysuccinamide, N-hydroxysulfosuccinimide (Sulfo-NHS) or mixture thereof.

The first aspect of the present invention provides an improved process for the preparation of amorphous form of 5-[[[(2S)-2-amino-3-[4-(aminocarbonyl)-2,6-dimethyl phenyl]-1-oxopropyl][(1S)-1-(4-phenyl-1H-imidazol-2yl)ethyl] amino]methyl]-2-methoxy benzoic acid compound of formula-1, comprising of following steps;

a) Reacting acid addition salts of (S)-methyl-2-methoxy-5-(((1-(4-phenyl-1H-imidazol-2-yl)ethyl)amino) methyl)benzoate compound of formula-2 with (S)-2-((tert-butoxy carbonyl)amino)-3-(4-carbamoyl-2,6- dimethylphenyl)propanoic acid compound of formula-3 in presence of a suitable coupling agent and a suitable base in a suitable solvent to provide methyl-5-(((2S)-2-((tert-butoxycarbonyl)amino)-3-(4-carbamoyl-2,6-dimethylphenyl)-N-((1S)-1-(4-phenyl-1H-imidazol-2-yl)ethyl)propanamido) methyl)-2-methoxy benzoate compound of formula-4, b) treating the compound of formula-4 with lithium hydroxide in a suitable solvent and followed by treating with sodium carbonate in a suitable solvent to provide 5-(((2S)-2-((tert-butoxycarbonyl)amino)-3-(4-carbamoyl-2,6-dimethylphenyl)-N-((1S)-1-(4-phenyl-1H-imidazol-2-yl)ethyl)propanamido)methyl)-2-methoxybenzoate sodium salt compound of formula-5a, c) optionally, purifying the compound of formula-5a with a suitable solvent, d) treating the compound of formula-5a with a suitable hydrochloric acid source in a suitable solvent and treating with a suitable base in a suitable solvent to provide 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxy benzoic acid compound of formula-1 or its solvates, e) dissolving the compound of formula-1 in a suitable solvent/mixture of solvents, followed by addition of resulting mixture to a suitable solvent at a suitable temperature to provide amorphous form of 5-[[[(2S)-2-amino-3-[4-(aminocarbonyl)-2,6-dimethyl phenyl]-1-oxopropyl][(1S)-1-(4-phenyl-1H-imidazol-2yl) ethyl]amino]methyl]-2-methoxy benzoic acid compound of formula-1.

Wherein, in step-a) the suitable coupling agent is selected from N,N'-dicyclohexyl carbodiimide (DCC), N,N'-diisopropylcarbodiimide (DIC), 1-ethyl-3-(3-dimethylamino propyl)carbodiimide HCl (EDC.HCl), alkyl or aryl chloroformates such as ethylchloro formate, benzylchloroformate, diphenylphosphoroazidate (DPPA), thionyl chloride, oxalyl chloride, phosphorous oxy chloride, phosphorouspentachloride, 4-methyl-2-oxopentanoyl chloride (i-BuCOCOCl), (Benzotriazol-1-yloxy)tripyrrolidinophosphoniumhexafluoro phosphate (PyBOP), methane sulfonyl chloride and the like optionally in combination with 1-hydroxy-7-azatriazole (HOAt), 1-Hydroxybenzotriazole (HOBt), 1-Hydroxy-1H-1,2,3-triazole-4-carboxylate (HOCt), N-hydroxysuccinamide (HOSu), N-hydroxysulfosuccinimide (Sulfo-NHS), 4-dimethylamino pyridine and the like and suitable base is selected from organic or inorganic base;

in step-d) the suitable hydrochloric acid source is selected from hydrochloric acid, aqueous hydrochloric acid, methanolic-HCl, ethanolic-HCl, IPA-HCl, hydrochloric acid gas and the suitable base is selected from organic base;

in step-a) to step-e) the suitable solvent is selected from alcohol solvents, ketone solvents, ester solvents, hydrocarbon solvents, polar aprotic solvents, ether solvents, nitrile solvents, chloro solvents and polar solvents like water or mixture thereof.

The preferred embodiment of the present invention provides an improved process for the preparation of amorphous form of 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxy benzoic acid compound of formula-1, comprising of following steps;

a) Reacting (S)-methyl-2-methoxy-5-(((1-(4-phenyl-1H-imidazol-2-yl)ethyl)amino) methyl)benzoate maleate salt compound of formula-2a with (S)-2-((tert-butoxycarbonyl)amino)-3-(4-carbamoyl-2,6-dimethylphenyl) propanoic acid compound of formula-3 in presence of 1-ethyl-3-(3-dimethylaminopropyl)carbodiimide-HCl, 1-hydroxybenzotriazole and diisopropylethylamine in acetonitrile to provide methyl-5-(((2S)-2-((tert-butoxycarbonyl)amino)-3-(4-carbamoyl-2,6-dimethylphenyl)-N-((1S)-1-(4-phenyl-1H-imidazol-2-yl)ethyl)propanamido)methyl)-2-methoxybenzoate compound of formula-4, b) treating the compound of formula-4 with lithium hydroxide in a mixture of isopropanol and water and followed by treating with sodium carbonate in a mixture of tetrahydrofuran, water and isopropanol to provide 5-(((2S)-2-((tert-butoxycarbonyl) amino)-3-(4-carbamoyl-2,6-dimethylphenyl)-N-((1S)-1-(4-phenyl-1H-imidazol-2-yl) ethyl)propanamido)methyl)-2-methoxybenzoate sodium salt compound of formula-5a, c) treating the compound of formula-5a with hydrochloric acid in acetonitrile and then followed by treating with triethyl amine in a mixture of water and 2-butanol to provide 5-[[[(2S)-2-amino-3-[4-(aminocarbonyl)-2,6-dimethylphenyl]-1-oxopropyl][(1S)-1-(4-phenyl-1H-imidazol-2yl )ethyl]amino]methyl]-2-methoxy benzoic acid 2-butanol solvate compound of formula-1, d) dissolving the 2-butanol solvate compound of formula-1 in a mixture of acetonitrile and water followed by addition of resulting mixture to a precooled water at 0-5° C. to provide amorphous form of 5-[[[(2S)-2-amino-3-[4-(aminocarbonyl)-2,6-dimethyl phenyl]-1-oxopropyl][(1S)-1-(4-phenyl-1H-imidazol-2yl)ethyl] amino]methyl]-2-methoxy benzoic acid compound of formula-1.

In an embodiment of the present invention, the compound of formula-4 can also be treated with a suitable base such as alkali or alkaline earth metal hydroxide or carbonates or bicarbonates or alkoxides that can form alkali or alkaline earth metal salts of compound of formula-5.

In an embodiment of the present invention the compound of formula-5a can be treated with a suitable acid in a suitable solvent to provide acid addition salts of compound of formula-1.

U.S. Pat. No. 7,741,356 B2 discloses process for the preparation of 5-(((2S)-2-(tert-butoxycarbonylamino)-3-(4-carbamoyl-2,6-dimethylphenyl)-N-((1S)-1-(4-phenyl-1H-imidazol-2-yl)ethyl)propanamido)methyl)-2-methoxybenzoic acid herein after referred to as "2-methoxybenzoic acid" by, reacting methyl-5-(((2S)-2-((tert-butoxycarbonyl) amino)-3-(4-carbamoyl-2,6-dimethylphenyl)-N-((1S)-1-(4-phenyl-1H-imidazol-2-yl)ethyl)propanamido) methyl)-2-methoxy benzoate compound of formula-4 with aqueous lithium hydroxide in the presence of tetrahydrofuran and methanol for longer hours and followed cumbersome work-up and tedious column chromatographic purification provides 2-methoxybenzoic acid with low yield.

The said process suffers from several draw backs such as utilizing multiple solvent system, lengthier reaction time and cumbersome work-up along with tedious column purification to isolate 2-methoxybenzoic acid with low yield. The said process also involves excess of solvents which leads to the generation of lot of spent solvents and solid waste which are difficult to dispose and which can lead to the pollution of the environment. Further, the said process increases the cost of the production and which is not recommended for commercial scale-up.

The present process is simple, eco-friendly and commercially viable, which involves lower mole ratio of lithium hydroxide in a single solvent and takes less time period for the completion of the reaction and further without any column purifications provides compound of formula-5a with high yield.

5-(((2S)-2-((tert-butoxycarbonyl)amino)-3-(4-carbamoyl-2,6-dimethylphenyl)-N-((1S)-1-(4-phenyl-1H-imidazol-2-yl)ethyl)propanamido)methyl)-2-methoxybenzoate sodium salt compound of formula-5a is having purity greater than 98% as measured by HPLC.

5-(((2S)-2-((tert-butoxycarbonyl)amino)-3-(4-carbamoyl-2,6-dimethylphenyl)-N-((1S)-1-(4-phenyl-1H-imidazol-2-yl)ethyl)propanamido)methyl)-2-methoxybenzoate sodium salt compound of formula-5a obtained according to the present invention is having Boc alcohol impurity; Boc diacid impurity; RS-Isomer, Boc isopropyl ester impurity, amine impurity, Boc ester impurity and amide impurity less than 0.05% as measured by HPLC.

| Name of the impurity & structure |
|---|
| 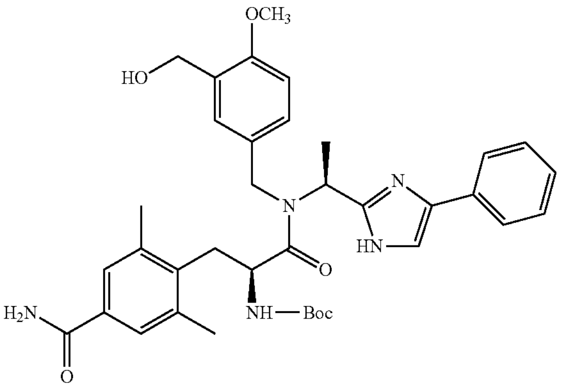 |
| tert-butyl ((S)-3-(4-carbamoyl-2,6-dimethylphenyl)-1-((3-(hydroxymethyl)-4-methoxybenzyl)((S)-1-(4-phenyl-1H-imidazol-2-yl)ethyl)amino)-1-oxopropan-2-yl) carbamate {Boc-Alcohol Impurity} |
| 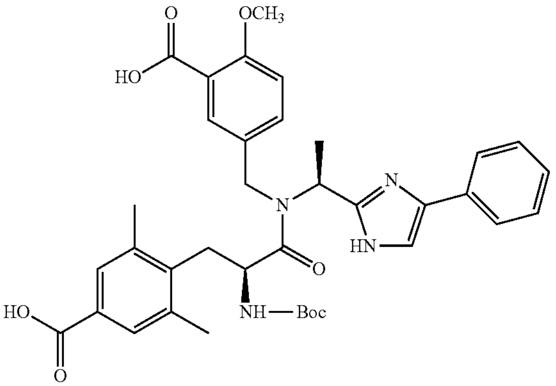 |
| 4-((2S)-2-((tert-butoxycarbonyl)amino)-3-((3-carboxy-4-methoxybenzyl)((1S)-1-(4-phenyl-1H-imidazol-2-yl) ethyl)amino)-3-oxopropyl)-3,5-dimethylbenzoic acid {Boc-Diacid impurity} |

-continued

| Name of the impurity & structure |
|---|
| 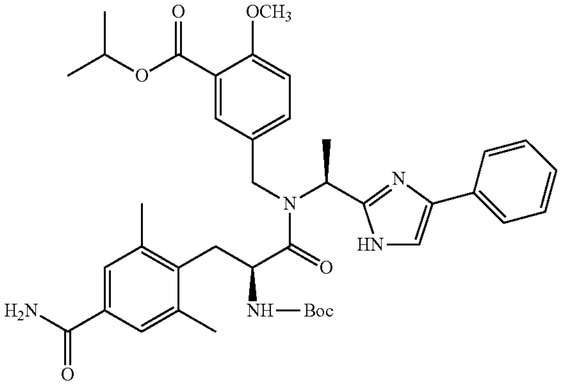 |
| Isopropyl5-(((2S)-2-((tert-butoxycarbonyl)amino)-3-(4 carbamoyl-2,6-dimethylphenyl)-N-((1S)-1-(4-phenyl-1H-imidazol-2-yl)ethyl)propanamido)methyl)-2-methoxy benzoate {Boc isopropyl ester impurity} |
| 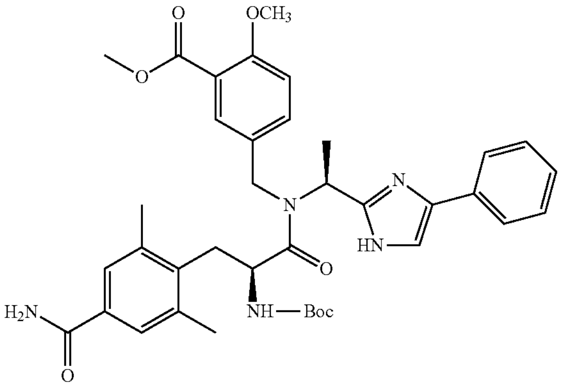 |
| Methyl5-(((2S)-2-((tert-butoxycarbonyl)amino)-3-(4-carbamoyl-2,6-dimethylphenyl)-N-((1S)-1-(4-phenyl-1H-imidazol-2-yl)ethyl)propanamido) methyl)-2-methoxybenzoate {Boc ester impurity} |
| 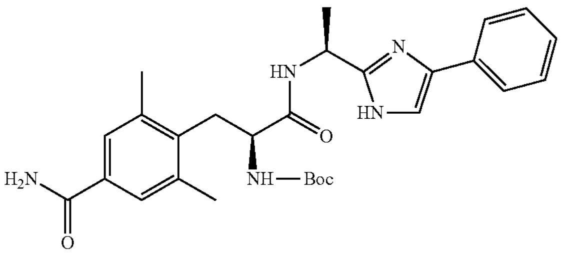 |
| Tert-butyl ((S)-3-(4-carbamoyl-2,6-dimethylphenyl)-1-oxo-1-(((S)-1-(4-phenyl-1H-imidazol-2-yl)ethyl) amino)propan-2-yl) carbamate {Amide Impurity} |

-continued

| Name of the impurity & structure |
| --- |
| 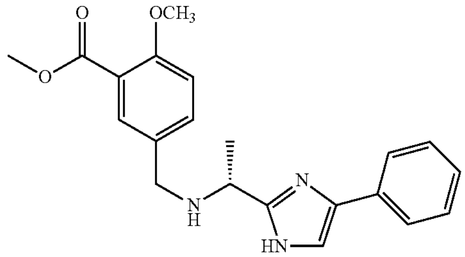 |
| (S)-Methyl 2-methoxy-5-(((1-(4-phenyl-1H-imidazol-2-yl)ethyl)amino)methyl)benzoate {Amine impurity} |

U.S. Pat. No. 7,994,206 B2 involves process for the preparation of compound of formula-1 by, reacting 2-methoxybenzoic acid with concentrated hydrochloric acid in acetone to provide hydrochloric acid salt of compound of formula-1, which is further neutralized by treating with aqueous sodium hydroxide to provide compound of formula-1 with low yield and purity.

On repetition of the above process, i.e. neutralization of hydrochloric acid salt of compound of formula-1 with sodium hydroxide, the compound of formula-1 is isolated as gummy solid with low yield and purity. In order to isolate compound of formula-1 as a free solid, required multiple number of purifications and thereby making the process more uneconomical and not suitable for commercial scale-up.

The inventors of the present invention have carried out the neutralization of hydrochloride salt of compound of formula-1 using different bases in various solvents. Surprisingly they found that the yield and purity of the final compound is very high whenever the hydrochloride salt of compound of formula-1 treated with organic base in presence of alcohol solvents.

The present inventors found that by carrying out the neutralization of hydrochloride salt of compound of formula-1 using a combination of triethyl amine and alcohol solvents preferably 2-butanol, produced the compound of formula-1 as a free solid with enhanced yield and purity. The same was illustrated in the following table:

| S. No | Input material | Base & solvent | Yield of Eluxadoline | Purity of Eluxadoline |
| --- | --- | --- | --- | --- |
| 01 | Eluxadoline HCl | TEA/2-butanol | 93.8% | 99.58% |
| 02 | -do- | TEA/n-propanol | 83.2% | 96.23% |

The second aspect of the present invention provides 5-[[[(2S)-2-amino-3-[4-(amino carbonyl)-2,6-dimethylphenyl]-1-oxopropyl][(1S)-1-(4-phenyl-1H-imidazol-2yl)ethyl]amino]methyl]-2-methoxybenzoic acid 2-butanol solvate compound of formula-1.

In an embodiment of the present invention provides crystalline form of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid 2-butanol solvate.

In another embodiment of the present invention provides crystalline form of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid 2-butanol solvate compound of formula-1 herein after designated as form-M and is characterized by, its powder X-Ray diffractogram having peaks at 6.2, 7.3, 8.9, 9.7, 10.3, 10.8, 12.1, 12.6, 13.6, 14.1, 14.8, 15.0, 15.6, 15.8, 17.6, 18.1, 18.7, 19.1, 19.4, 20.2, 21.1, 21.9, 22.5, 23.1, 24.0, 24.6, 25.2, 27.7, 28.0, 31.6 and 32.6±0.2 degrees of two-theta as depicted in FIG. 1.

The crystalline form-M of compound of formula-1 obtained according to the present invention is useful in the preparation of pure 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1.

The another embodiment of the present invention provides a process for the preparation of crystalline form-M of 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxy benzoic acid 2-butanol solvate compound of formula-1, comprising of;

a) Dissolving 5-[[[(2S)-2-amino-3-[4-(aminocarbonyl)-2,6-dimethylphenyl]-1-oxo propyl][(1S)-1-(4-phenyl-1H-imidazol-2yl)ethyl]amino]methyl]-2-methoxy benzoic acid hydrochloride salt compound of formula-1a in 2-butanol or aqueous 2-butanol,
b) adding a suitable organic base to the reaction mixture,
c) stirring the reaction mixture,
d) filtering the precipitated solid and drying to get the crystalline form-M of 5-(((S)-2-amino-3-(4-carbamoyl-2,6-dimethylphenyl)-N—((S)-1-(4-phenyl-1H-imidazol-2-yl) ethyl)propanamido)methyl)-2-methoxy benzoic acid 2-butanol solvate compound of formula-1.

The preferred embodiment of the present invention provides a process for the preparation of crystalline form-M of 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxy benzoic acid 2-butanol solvate compound of formula-1, comprising of;

a) Dissolving 5-[[[(2S)-2-amino-3-[4-(aminocarbonyl)-2,6-dimethylphenyl]-1-oxo propyl][(1S)-1-(4-phenyl-1H-imidazol-2yl)ethyl]amino]methyl]-2-methoxy benzoic acid hydrochloride salt compound of formula-1a in a mixture of water and 2-butanol,
b) adding triethyl amine to the reaction mixture,
c) stirring the reaction mixture,
d) filtering the precipitated solid and drying to get the crystalline form-M of 5-(((S)-2-amino-3-(4-carbamoyl-2,6-dimethylphenyl)-N—((S)-1-(4-phenyl-1H-imidazol-2-yl) ethyl)propanamido)methyl)-2-methoxy benzoic acid 2-butanol solvate compound of formula-1.

The third aspect of the present invention provides a new, accurate and sensitive HPLC method for analyzing 5-[[[(2S)-2-amino-3-[4-(aminocarbonyl)-2,6-dimethylphenyl]-1-oxo propyl][(1S)-1-(4-phenyl-1H-imidazol-2yl)ethyl]amino]methyl]-2-methoxybenzoic acid compound of formula-1 and it intermediates.

The technique of choice for the analysis of APIs or pharmaceutical compositions (e.g. a tablet or capsule) is usually High Performance liquid Chromatography (HPLC) coupled with a UV-Visible detector. The API and the impurities present, if any, are separated on the HPLC stationary phase and they can be detected and quantified using their response obtained from the UV-Visible detector.

The likely impurities in APIs and pharmaceutical compositions include residual quantities of synthetic precursors (intermediates), by-products which arise during the synthesis of the API, residual solvents, isomers of the API (e.g. geometrical isomers, diastereomers or enantiomers), contaminants which are present in materials used in the synthesis of the API or in the preparation of the pharmaceutical composition, and unidentified adventitious substances. Other impurities which may appear on storage include degradants of the API, for instance formed by hydrolysis or oxidation.

However, the current HPLC methods are not suitable for the detection and estimation of all total synthetic impurities and other related substances that are present, especially with respect to known and unknown impurities that are present in Eluxadoline. Studies by the present inventors have culminated in the development and validation of a new, accurate, efficient, reproducible and simple HPLC method for the analysis of Eluxadoline, particularly with respect to the related substances formed during the synthetic process, whilst avoiding the typical problems associated with the prior art methods.

In an embodiment of the present invention provides a new, accurate and sensitive HPLC method for the analyzing of 5-[[[(2S)-2-amino-3-[4-(aminocarbonyl)-2,6-dimethyl phenyl]-1-oxopropyl][(1S)-1-(4-phenyl-1H-imidazol-2yl) ethyl]amino]methyl]-2-methoxy benzoic acid compound of formula-1.

In another embodiment of the present invention the purity of the 5-[[[(2S)-2-amino-3-[4-(aminocarbonyl)-2,6-dimethylphenyl]-1-oxopropyl][(1S)-1-(4-phenyl-1H-imidazol-2yl) ethyl]amino]methyl]-2-methoxy benzoic acid compound of formula-1 can be determined using chiral HPLC method using Lux i-Cellulose-5 (Make: Phenomenex), Chiralpak IC-3 column.

Figure 2:
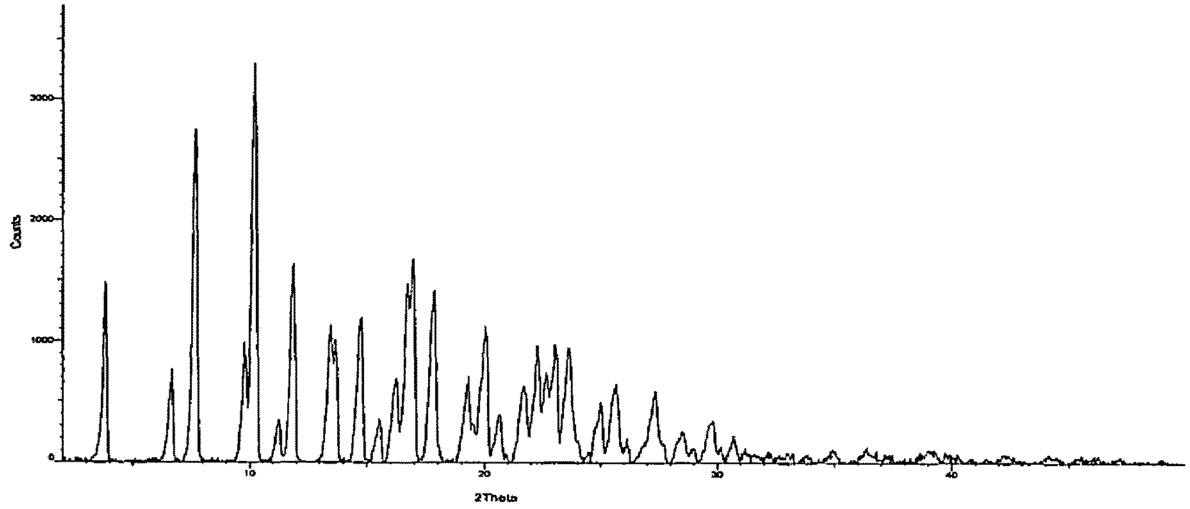
FIG. 2: Illustrates the PXRD pattern of crystalline form-S1 of 5-(((2S)-2-((tert-butoxy carbonyl)amino)-3-(4-carbamoyl-2,6-dimethylphenyl)-N-((1S)-1-(4-phenyl-1H-imidazol-2-yl) ethyl)propanamido)methyl)-2-methoxy benzoate lithium salt compound of formula-5b.

The fourth aspect of the present invention provides crystalline form-S1 of 5-(((S)-2-((tert-butoxycarbonyl)amino)-3-(4-carbamoyl-2,6-dimethylphenyl)-N—((S)-1-(4-phenyl-1H-imidazol-2-yl)ethyl)propanamido)methyl)-2-methoxy benzoate lithium salt compound of formula-5b and the P-XRD pattern is depicted in FIG. 2.

In another embodiment of the present invention provides a process for the preparation of crystalline form-S1 of 5-(((2S)-2-((tert-butoxycarbonyl)amino)-3-(4-carbamoyl-2,6-di methylphenyl)-N-((1S)-1-(4-phenyl-1H-imidazol-2-yl) ethyl)propanamido)methyl)-2-methoxy benzoate lithium salt compound of formula-5b, comprising of:

a) Adding a suitable solvent to methyl 5-(((2S)-2-(tert-butoxycarbonylamino)-3-(4-carbamoyl-2,6-dimethylphenyl)-N-((1S)-1-(4-phenyl-1H-imidazol-2-yl) ethyl) propanamido)methyl)-2-methoxybenzoate compound of formula-4,
b) cooling the reaction mixture,
c) adding aqueous lithium hydroxide to the reaction mixture,
d) heating and stirring the reaction mixture at a suitable temperature,
e) cooling the reaction mixture and optionally purifying the obtained compound using a suitable solvent to provide crystalline form-S1 of 5-(((2S)-2-((tert-butoxycarbonyl) amino)-3-(4-carbamoyl-2,6-dimethylphenyl)-N-((1S)-1-(4-phenyl-1H-imidazol-2-yl) ethyl)propanamido)methyl)-2-methoxy benzoate lithium salt compound of formula-5b.

Wherein, in step-b) the suitable temperature is ranging from 0° C. to 10° C.;
in step-d) the suitable temperature is ranging from 25° C. to 65° C.;
in step-a) and e) the suitable solvent is selected from alcohol solvents, ketone solvents, ester solvents, hydrocarbon solvents, polar aprotic solvents, ether solvents, nitrile solvents, chloro solvents and polar solvents like water or mixture thereof.

The preferred embodiment of the present invention provides a process for the preparation of crystalline form-S1 of 5-(((2S)-2-((tert-butoxycarbonyl)amino)-3-(4-carbamoyl -2,6-dimethylphenyl)-N-((1S)-1-(4-phenyl-1H-imidazol-2-yl)ethyl)propanamido)methyl)-2-methoxy benzoate lithium salt compound of formula-5b, comprising of:

a) Adding isopropanol to methyl 5-(((2S)-2-(tert-butoxycarbonylamino)-3-(4-carbamoyl-2,6-dimethylphenyl)-N-((1S)-1-(4-phenyl-1H-imidazol-2-yl)ethyl)propanamido) methyl)-2-methoxybenzoate compound of formula-4,
b) cooling the reaction mixture to 0-5° C.,
c) adding aqueous lithium hydroxide to the reaction mixture,
d) raising the temperature of the reaction mixture to 25-30° C. and stirring the reaction mixture,
e) heating the reaction mixture to 40-45° C. and stirring the reaction mixture,
f) cooling the reaction mixture and adding isopropanol to the reaction mixture to provide crystalline form-S1 of 5-(((2S)-2-((tert-butoxycarbonyl)amino)-3-(4-carbamoyl-2,6-dimethylphenyl)-N-((1S)-1-(4-phenyl-1H-imidazol-2-yl)ethyl)propanamido)methyl)-2-methoxy benzoate lithium salt compound of formula-5b.

The fifth aspect of the present invention provides 5-(((2S)-2-((tert-butoxycarbonyl) amino)-3-(4-carbamoyl-2,6-dimethylphenyl)-N-((1S)-1-(4-phenyl-1H-imidazol-2-yl) ethyl) propanamido)methyl)-2-methoxy benzoate sodium salt compound of formula-5a.

Figure 3:
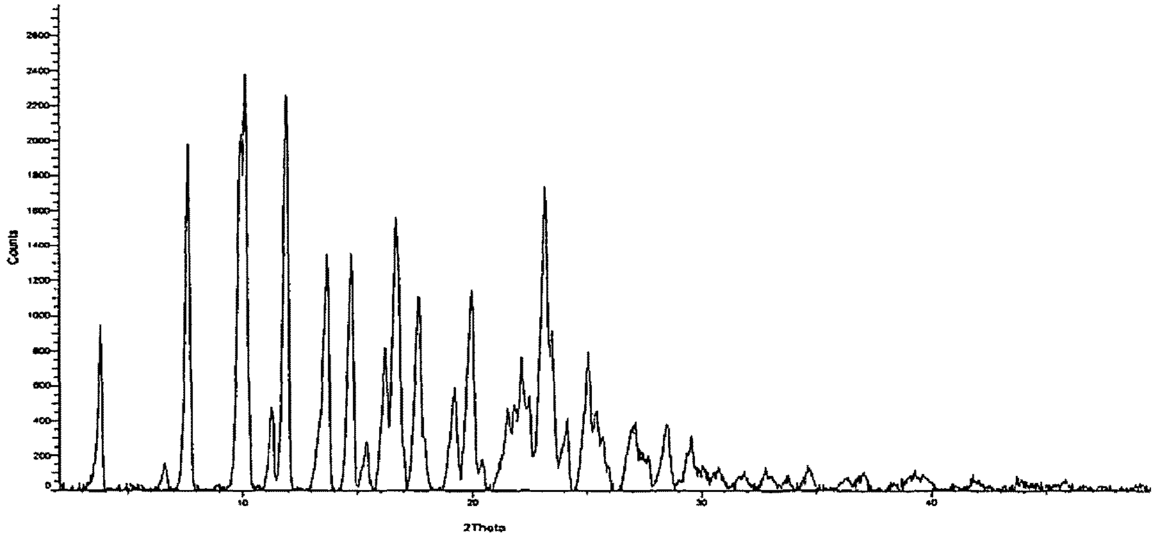

The another embodiment of the present invention provides crystalline form of 5-(((2S)-2-((tert-butoxycarbonyl) amino)-3-(4-carbamoyl-2,6-dimethylphenyl)-N-((1S)-1-(4-phenyl-1H-imidazol-2-yl)ethyl)propanamido)methyl)-2-methoxy benzoate sodium salt compound of formula-5a, herein after designated as form-S2 and the P-XRD pattern is depicted in FIG. 3.

The another embodiment of the present invention provides process for the preparation of crystalline form-S2 of 5-(((2S)-2-((tert-butoxycarbonyl)amino)-3-(4-carbamoyl-2,6-di methylphenyl)-N-((1S)-1-(4-phenyl-1H-imidazol-2-yl) ethyl)propanamido)methyl)-2-methoxy benzoate sodium salt compound of formula-5a, comprising of:

a) Adding a suitable solvent to 5-(((2S)-2-((tert-butoxycarbonyl)amino)-3-(4-carbamoyl-2,6-dimethylphenyl)-N-((1S)-1-(4-phenyl-1H-imidazol-2-yl)ethyl)propanamido) methyl)-2-methoxy benzoate lithium salt,
b) adding a suitable sodium source to the reaction mixture,
c) heating and stirring the reaction mixture,
d) cooling the reaction mixture and isolating the compound,
e) optionally purifying the obtained compound using a suitable solvent to provide crystalline form-S2 of 5-(((2S)-2-((tert-butoxycarbonyl) amino)-3-(4-carbamoyl-2,6-dimethylphenyl)-N-((1S)-1-(4-phenyl-1H-imidazol-2-yl) ethyl)propanamido)methyl)-2-methoxy benzoate sodium salt compound of formula-5a.

Wherein, in step-b) the suitable sodium source is selected from sodium carbonate, sodium bicarbonate, sodium hydroxide, sodium methoxide;
in step-c) the suitable temperature is ranging from ambient temperature to reflux temperature of the solvent used in the reaction;

in step-d) the suitable temperature is ranging from 20-35° C.;

in step-a) and e) the suitable solvent is same as defined in step-a) of the fourth aspect of the present invention.

The preferred embodiment of the present invention provides process for the preparation of crystalline form-S2 of 5-(((2S)-2-((tert-butoxycarbonyl)amino)-3-(4-carbamoyl-2,6-dimethylphenyl)-N-((1S)-1-(4-phenyl-1H-imidazol-2-yl) ethyl)propanamido) methyl)-2-methoxy benzoate sodium salt compound of formula-5a, comprising of:

a) Adding a mixture of tetrahydrofuran and water to 5-(((2S)-2-((tert-butoxycarbonyl) amino)-3-(4-carbamoyl-2,6-dimethylphenyl)-N-((1S)-1-(4-phenyl-1H-imidazol-2-yl) ethyl)propanamido) methyl)-2-methoxy benzoate lithium salt,
b) adding sodium carbonate to the reaction mixture,
c) heating the reaction mixture to 40-45° C. and stirring the reaction mixture,
d) cooling the reaction mixture to 25-30° C.,
e) isolating the compound by adding isopropanol to the reaction mixture,
f) purifying the obtained compound by, adding a mixture of tetrahydrofuran and water and then adding isopropanol to the obtained reaction mixture to provide crystalline form-S2 of 5-(((2S)-2-((tert-butoxycarbonyl)amino)-3-(4-carbamoyl-2,6-dimethyl phenyl)-N-((1S)-1-(4-phenyl-1H-imidazol-2-yl)ethyl)propanamido)methyl)-2-methoxy benzoate sodium salt compound of formula-5a.

The 5-(((2S)-2-((tert-butoxycarbonyl)amino)-3-(4-carbamoyl-2,6-dimethylphenyl)-N-((1S)-1-(4-phenyl-1H-imidazol-2-yl)ethyl)propanamido)methyl)-2-methoxybenzoate sodium salt compound of formula-5a can be prepared by, hydrolyzing methyl 5-(((2S)-2-(tert-butoxy carbonylamino)-3-(4-carbamoyl-2,6-dimethylphenyl)-N-((1S)-1-(4-phenyl-1H-imidazol-2-yl) ethyl)propanamido)methyl)-2-methoxybenzoate compound of formula-4 using a suitable sodium source in a suitable solvent.

The crystalline form-S1 and form-S2 of corresponding salts of 5-(((2S)-2-((tert-butoxy carbonyl)amino)-3-(4-carbamoyl-2,6-dimethylphenyl)-N-((1S)-1-(4-phenyl-1H-imidazol-2-yl)ethyl)propanamido)methyl)-2-methoxy benzoate are useful in the preparation of pure compound of formula-1.

5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 obtained according to the present invention having the following impurities less than 0.05% as measured by HPLC.

a) 5-(((2R)-2-Amino-3-(4-carbamoyl-2,6-dimethylphenyl)-N-((1S)-1-(4-phenyl-1H-imidazol-2-yl)ethyl)propanamido)methyl)-2-methoxy benzoic acid {diastereomers impurity},
b) 4-((2S)-2-Amino-3-((3-carboxy-4-methoxybenzyl)((1S)-1-(4-phenyl-1H-imidazol-2-yl)ethyl) amino)-3-oxopropyl)-3,5-dimethyl benzoic acid {diacid impurity},
c) Isopropyl 5-(((2S)-2-amino-3-(4-carbamoyl-2,6-dimethylphenyl)-N-((1S)-1-(4-phenyl-1H-imidazol-2-yl)ethyl) propanamido)methyl)-2-methoxy benzoate {isopropyl impurity},
d) Sec-butyl 5-(((2S)-2-amino-3-(4-carbamoyl-2,6-dimethylphenyl)-N-((1S)-1-(4-phenyl-1H-imidazol-2-yl)ethyl) propanamido)methyl)-2-methoxy benzoate {butyl ester impurity}, and
e) 5-(((2R)-2-Amino-3-(4-carbamoyl-2,6-dimethylphenyl)-N-((1R)-1-(4-phenyl-1H-imidazol-2-yl)ethyl)propanamido)methyl)-2-methoxybenzoic acid {Enantiomer impurity}.

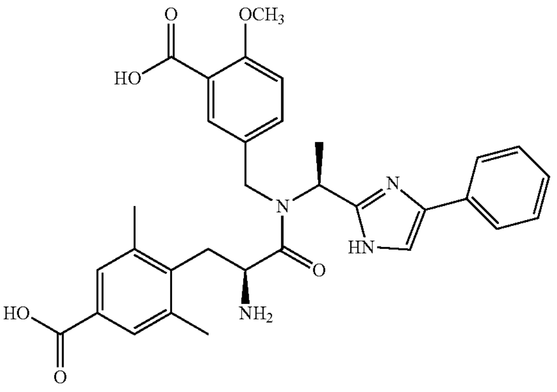

{Diacid Impurity}

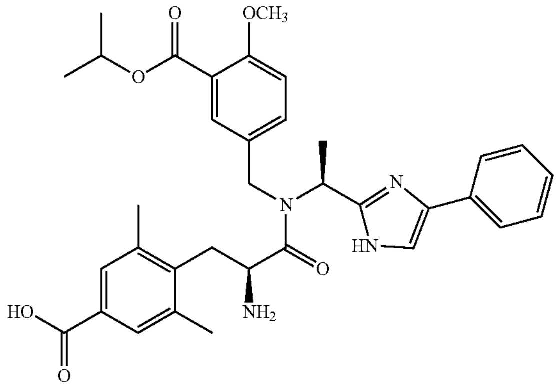

{Isopropyl ester impurity}

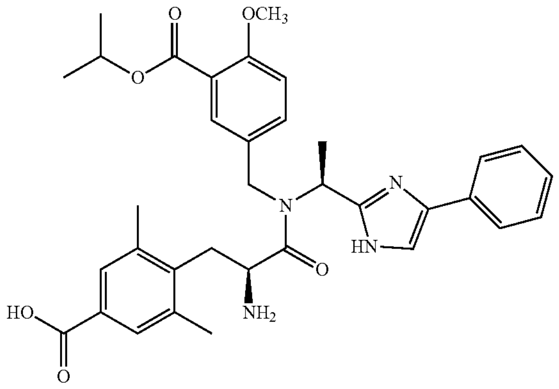

{Butyl ester impurity}

-continued

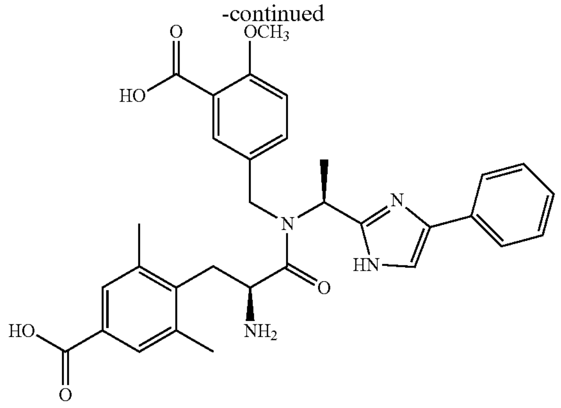

{Enantiomer impurity}

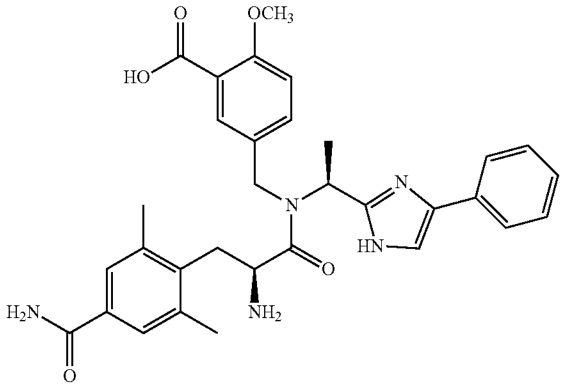

{Diastereomer impurity}

5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 obtained according to the present invention having purity greater than 99.85%, preferably greater than 99.95%, most preferably greater than 99.98% as measured by HPLC.

The sixth aspect of the present invention provides a process for the preparation of amorphous form of 5-[[[(2S)-2-amino-3-[4-(aminocarbonyl)-2,6-dimethylphenyl]-1-oxo propyl][(1S)-1-(4-phenyl-1H-imidazol-2yl)ethyl]amino] methyl]-2-methoxybenzoic acid compound of formula-1, comprising of following steps;

a) Adding 5-[[[(2S)-2-amino-3-[4-(aminocarbonyl)-2,6-dimethylphenyl]-1-oxopropyl] [(1S)-1-(4-phenyl-1H-imidazol-2yl)ethyl]amino]methyl]-2-methoxybenzoic acid 2-butanol solvate compound of formula-1 to a suitable solvent,
b) heating the reaction mixture,
c) adding the above reaction mixture to a pre-cooled solvent,
d) stirring the reaction mixture,
e) filtering the precipitated solid and drying to get amorphous form of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1.

Wherein, in step-a) and c) the suitable solvent is selected from alcohol solvents, ketone solvents, ester solvents, hydrocarbon solvents, polar aprotic solvents, ether solvents, nitrile solvents, chloro solvents and polar solvents like water or mixture thereof;

in step-b) the suitable temperature is ranging from 25° C. to the reflux temperature of the solvent used in the reaction;

in step-c) the suitable temperature is ranging from −50° C. to 0° C.

The preferred embodiment of the present invention provides a process for the preparation of amorphous form of 5-[[[(2S)-2-amino-3-[4-(aminocarbonyl)-2,6-dimethyl phenyl]-1-oxopropyl][(1S)-1-(4-phenyl-1H-imidazol-2yl)ethyl] amino]methyl]-2-methoxy benzoic acid compound of formula-1, comprising of following steps;

a) Adding 5-[[[(2S)-2-amino-3-[4-(aminocarbonyl)-2,6-dimethylphenyl]-1-oxopropyl] [(1S)-1-(4-phenyl-1H-imidazol-2yl)ethyl]amino]methyl]-2-methoxybenzoic acid 2-butanol solvate compound of formula-1 to a mixture of acetonitrile and water,
b) heating the reaction mixture to 40-45° C.,
c) adding the above reaction mixture to a pre-cooled acetonitrile at 0-5° C.,
d) stirring the reaction mixture, filtering the precipitated solid and drying to get amorphous form of 5-[[[(2S)-2-amino-3-[4-(aminocarbonyl)-2,6-dimethylphenyl]-1-oxopropyl] [(1S)-1-(4-phenyl-1H-imidazol-2yl) ethyl]amino]methyl]-2-methoxy benzoic acid compound of formula-1.

The preferred embodiment of the present invention provides a process for the preparation of amorphous form of 5-[[[(2S)-2-amino-3-[4-(aminocarbonyl)-2,6-dimethyl phenyl]-1-oxopropyl][(1S)-1-(4-phenyl-1H-imidazol-2yl)ethyl] amino]methyl]-2-methoxy benzoic acid compound of formula-1, comprising of following steps;

a) Adding 5-[[[(2S)-2-amino-3-[4-(aminocarbonyl)-2,6-dimethylphenyl]-1-oxopropyl] [(1S)-1-(4-phenyl-1H-imidazol-2yl)ethyl]amino]methyl]-2-methoxybenzoic acid 2-butanol solvate compound of formula-1 to a mixture of acetonitrile and water,
b) heating the reaction mixture to 40-45° C.,
c) adding the above reaction mixture to a pre-cooled acetone (or) heptane at 0-5° C.,
d) stirring the reaction mixture, filtering the precipitated solid and drying to get amorphous form of 5-[[[(2S)-2-amino-3-[4-(aminocarbonyl)-2,6-dimethylphenyl]-1-oxopropyl][(1S)-1-(4-phenyl-1H-imidazol-2yl) ethyl]amino]methyl]-2-methoxy benzoic acid compound of formula-1.

The another preferred embodiment of the present invention provides a process for the preparation of amorphous form of 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxy benzoic acid compound of formula-1, comprising of following steps;

a) Adding 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid 2-butanol solvate compound of formula-1 to a mixture of acetonitrile, methanol and water,
b) adding the above reaction mixture to a precooled water at 0° C. to 5° C.,
c) stirring the reaction mixture, filtering the precipitated solid and drying to get amorphous form of 5-[[[(2S)-2-amino-3-[4-(aminocarbonyl)-2,6-dimethylphenyl]-1-oxopropyl][(1S)-1-(4-phenyl-1H-imidazol-2yl) ethyl]amino]methyl]-2-methoxy benzoic acid compound of formula-1.

Figure 5:
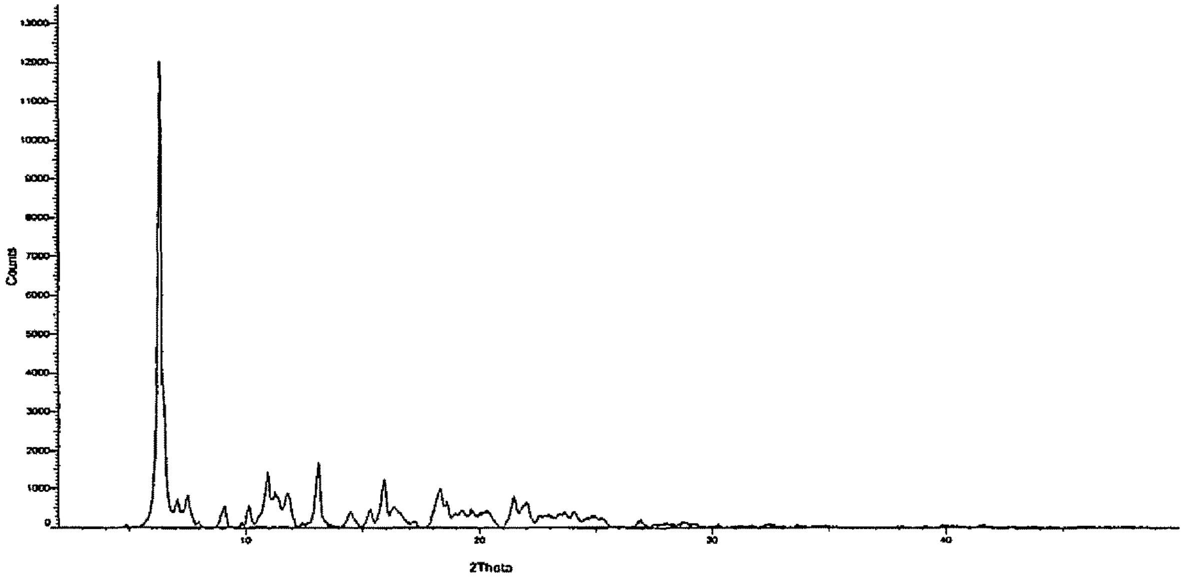
FIG. 5: Illustrates the PXRD pattern of crystalline form-N of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1.

The seventh aspect of the present invention provides a novel crystalline form-N of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1 characterized by its powder X-Ray diffractogram having peaks at 6.3, 7.0, 7.5, 9.0, 10.1, 10.9, 11.3, 11.8, 13.1, 14.5, 15.3, 15.9, 16.3, 18.3, 18.5, 19.2, 19.6, 20.2, 21.4, 21.9, 23.5 and 24.0±0.2 degrees of two-theta and the P-XRD pattern was depicted in FIG. 5.

In another embodiment of the present invention provides a process for the preparation of crystalline form-N of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1, comprising of:

a) Adding a suitable solvent to 5-[[[(2S)-2-amino-3-[4-(aminocarbonyl)-2,6-dimethyl phenyl]-1-oxopropyl][(1S)-1-(4-phenyl-1H-imidazol-2yl )ethyl]amino]methyl]-2-methoxy benzoic acid 2-butanol solvate,
b) heating and stirring the reaction mixture,
c) cooling the reaction mixture,
d) stirring the reaction mixture, filtering the solid and drying to get the crystalline form-N of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid.

Wherein, in step-a) the suitable solvent is selected from alcohol solvents, ketone solvents, ester solvents, hydrocarbon solvents, polar aprotic solvents, ether solvents, nitrile solvents, chloro solvents and polar solvents like water or mixture thereof;

in step-b) the suitable temperature is ranging from 25° C. to reflux temperature of the solvent used in the reaction.

The preferred embodiment of the present invention provides a process for the preparation of crystalline form-N of 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxy benzoic acid compound of formula-1, comprising of:

a) Adding methanol to 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxy benzoic acid 2-butanol solvate,
b) heating and stirring the reaction mixture at 40-45° C.,
c) cooling the reaction mixture to 25-30° C.,
d) stirring the reaction mixture, filtering the solid and drying to get the crystalline form-N of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid.

The crystalline form-N of compound of formula-1 obtained according to the present invention is useful in the preparation of pure 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1.

Figure 6:
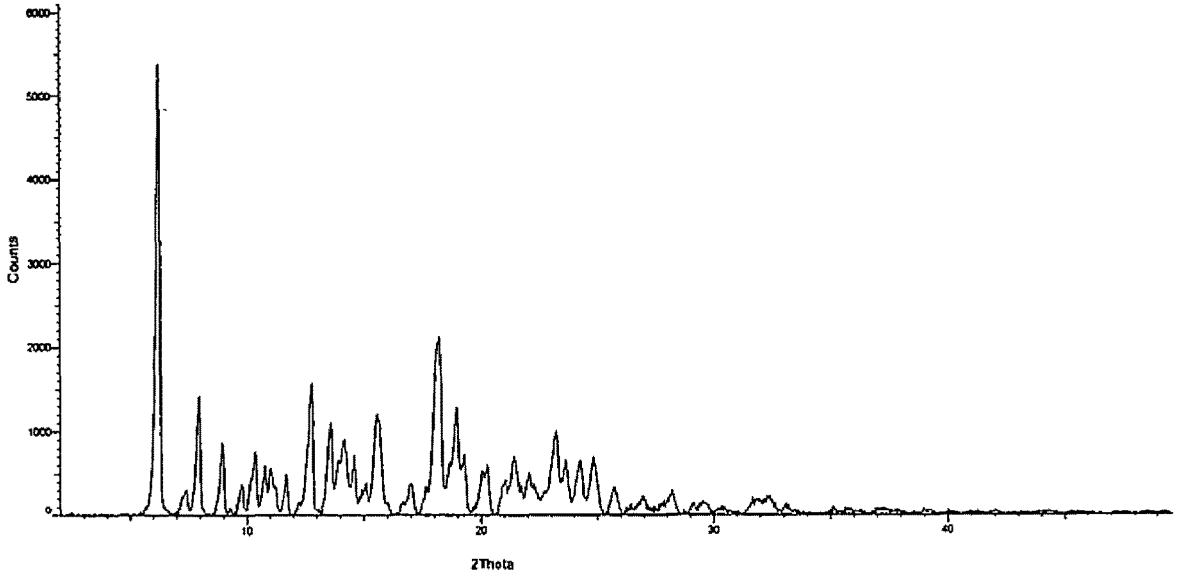
FIG. 6: Illustrates the PXRD pattern of crystalline form-M1 of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1.

The eighth aspect of the present invention provide a novel crystalline form-M1 of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1 characterized by its powder X-Ray diffractogram having peaks at 6.2, 7.3, 7.9, 8.9, 9.7, 10.3, 10.7, 11.0, 11.1, 11.7, 12.7, 13.5, 13.9, 14.1, 14.5, 15.0, 15.6, 16.7, 17.0, 17.6, 18.1, 18.6, 18.9, 19.2, 20.1, 20.3, 21.0, 21.4, 22.0, 23.2, 23.6, 24.2, 24.8, 25.7, 26.9, 28.2, 29.6 and 32.3±0.2 degrees of two-theta and the P-XRD pattern is depicted in FIG. 6.

In another embodiment of the present invention provides a process for the preparation of crystalline form-M1 of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1, comprising of:

a) Adding a suitable solvent to 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxybenzoic acid,
b) heating and stirring the reaction mixture,
c) cooling the reaction mixture,
d) stirring the reaction mixture, filtering the solid and drying to get the crystalline form-M1 of 5-[[[(2S)-2-amino-3-[4-(aminocarbonyl)-2,6-dimethylphenyl]-1-oxopropyl] [(1S)-1-(4-phenyl-1H-imidazol-2yl)ethyl]amino]methyl]-2-methoxybenzoic acid.

Wherein, in step-a) the suitable solvent is same as defined in step-a) of the seventh aspect of the present invention;

in step-b) the suitable temperature is ranging from 25° C. to reflux temperature of the solvent used in the reaction.

The preferred embodiment of the present invention provides a process for the preparation of crystalline form-M1 of 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxy benzoic acid compound of formula-1, comprising of:

a) Adding propylene glycol to 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxy benzoic acid 2-butanol solvate,
b) heating the reaction mixture to 60-65° C. and stirring the reaction mixture,
c) cooling the reaction mixture to 25-30° C.,
d) stirring the reaction mixture, filtering the solid and drying to get the crystalline form-M1 of 5-[[[(2S)-2-amino-3-[4-(aminocarbonyl)-2,6-dimethylphenyl]-1-oxopropyl] [(1S)-1-(4-phenyl-1H-imidazol-2yl)ethyl]amino]methyl]-2-methoxybenzoic acid.

Figure 7:
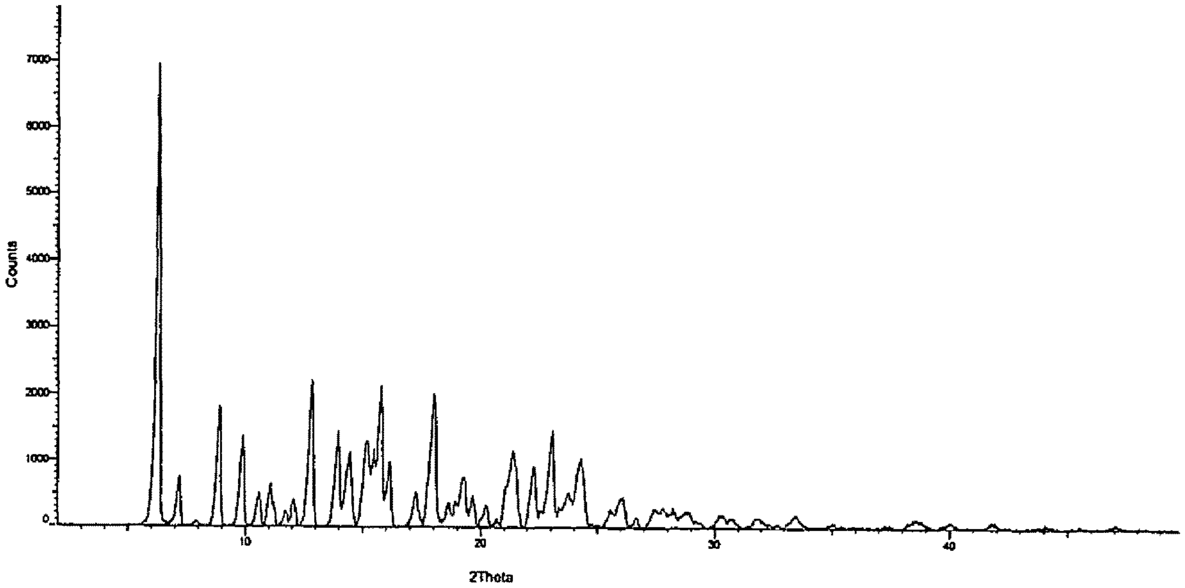
FIG. 7: Illustrates the PXRD pattern of crystalline form-M2 of 5-[[[(2S)-2-amino-3-[4-(aminocarbonyl)-2,6-dimethylphenyl]-1-oxopropyl][(1S)-1-(4-phenyl-1H-imidazol-2yl) ethyl]amino]methyl]-2-methoxybenzoic acid compound of formula-1.

The ninth aspect of the present invention provide a novel crystalline form-M2 of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1 characterized by its powder X-Ray diffractogram having peaks at 6.3, 7.1, 8.8, 9.8, 10.5, 11.0, 11.7, 12.0, 12.8, 13.9, 14.4, 15.1, 15.4, 15.7, 16.1, 17.2, 18.0, 18.6, 18.9, 19.2, 19.6, 20.2, 21.1, 21.3, 21.5, 22.2, 23.0, 23.4, 23.7, 24.3, 25.5, 26.0, 27.4, 27.8, 28.2, 28.9, 30.3 and 33.4±0.2 degrees of two-theta and the P-XRD pattern is depicted in FIG. 7.

In another embodiment of the present invention provides a process for the preparation of crystalline form-M2 of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid compound of formula-1, comprising of:

a) Adding a suitable solvent to 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxybenzoic acid 2-butanol solvate,
b) heating and stirring the reaction mixture,
c) cooling the reaction mixture,
d) stirring the reaction mixture, filtering the solid and drying to get the crystalline form-M2 of 5-[[[(2S)-2-amino-3-[4-(aminocarbonyl)-2,6-dimethylphenyl]-1-oxopropyl] [(1S)-1-(4-phenyl-1H-imidazol-2yl)ethyl]amino]methyl]-2-methoxybenzoic acid.

Wherein, in step-a) the suitable solvent is same as defined in step-a) of the seventh aspect of the present invention;

in step-b) the suitable temperature is ranging from 25° C. to reflux temperature of the solvent used in the reaction.

The preferred embodiment of the present invention provides a process for the preparation of crystalline form-M2 of 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxy benzoic acid compound of formula-1, comprising of:

a) Adding anisole to 5-[[[(2S)-2-amino-3-[4-(aminocarbonyl)-2,6-dimethyl phenyl]-1-oxopropyl][(1S)-1-(4-phenyl-1H-imidazol-2yl)ethyl]amino]methyl]-2-methoxy benzoic acid 2-butanol solvate, b) heating the reaction mixture to 40-45° C. and stirring the reaction mixture, c) cooling the reaction mixture to 25-30° C., d) stirring the reaction mixture, filtering the solid and drying to get the crystalline form-M2 of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid.

The tenth aspect of the present invention relates to acid addition salts of (S)-methyl-2-methoxy-5-(((1-(4-phenyl-1H-imidazol-2-yl)ethyl)amino)methyl)benzoate compound of formula-2 and process for their preparation, which comprises of reacting the compound of formula-2 with a suitable acid in a suitable solvent to provide acid addition salt of compound of formula-2.

Wherein, the acid addition salts and a suitable acid is selected from inorganic acids, such as hydrobromic acid, hydrochloric acid, sulfuric acid, nitric acid or phosphoric acid; and organic acids such as oxalic acid, maleic acid, malonic acid, tartaric acid, fumaric acid, citric acid, malic acid, succinic acid, mandelic acid, lactic acid, acetic acid, propionic acid, 2-chloromandelate, p-toluene sulfonic acid, ethane-1,2-disulfonic acid, camphor sulfonic acid, ethane sulfonic acid, methane sulfonic acid, naphthalene-2-sulfonic acid, benzene sulfonic acid, adipic acid, glutaric acid, glutamic acid, palmitic acid or aspartic acid;

The suitable solvent is selected from hydrocarbon solvents, ketone solvents, alcohol solvents, ether solvents, chloro solvents, nitrile solvents, ester solvents, polar aprotic solvents and polar solvent like water or mixture thereof.

Figure 8:
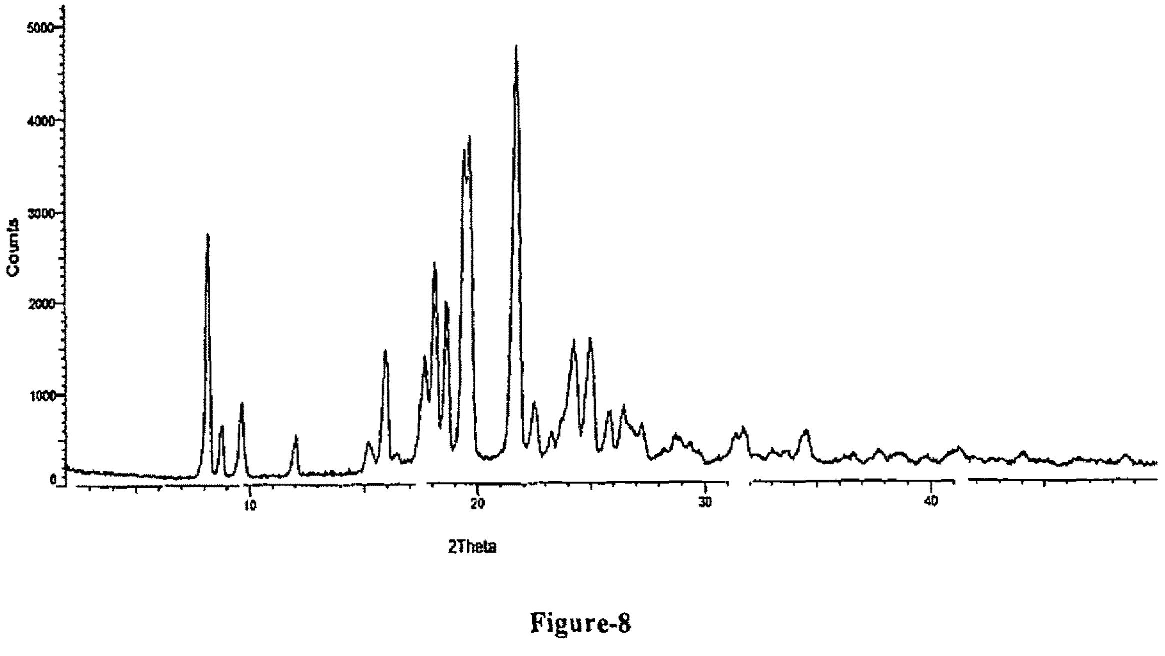

The eleventh aspect of the present invention relates to novel crystalline form-M of (S)-methyl-2-methoxy-5-(((1-(4-phenyl-1H-imidazol-2-yl)ethyl)amino)methyl)benzoate maleate salt compound of formula-2a characterized by its X-ray powder diffractogram having peaks at 8.1, 8.7, 9.6, 12.0, 15.2, 15.9, 17.6, 18.1, 18.6, 19.4, 19.6, 21.7, 22.5, 24.2, 24.9, 25.8, 26.4, 27.2, 28.7, 31.6 and 34.4±0.2 degrees two-theta as illustrated in FIG. 8.

Further embodiment of the present invention provides a process for the preparation of crystalline form-M of (S)-methyl-2-methoxy-5-(((1-(4-phenyl-1H-imidazol-2-yl)ethyl) amino)methyl)benzoate maleate salt compound of formula-2a comprising of the following steps:

a) Adding isopropanol to (S)-methyl-2-methoxy-5-(((1-(4-phenyl-1H-imidazol-2-yl) ethyl)amino)methyl)benzoate compound of formula-2.

b) adding maleic acid to the reaction mixture.

c) stirring the reaction mixture at 25-30° C.

d) filtering the precipitated solid to get the crystalline form-M of (S)-methyl-2-methoxy-5-(((1-(4-phenyl-1H-imidazol-2-yl)ethyl)amino)methyl)benzoate maleate salt compound of formula-2a.

Figure 9:
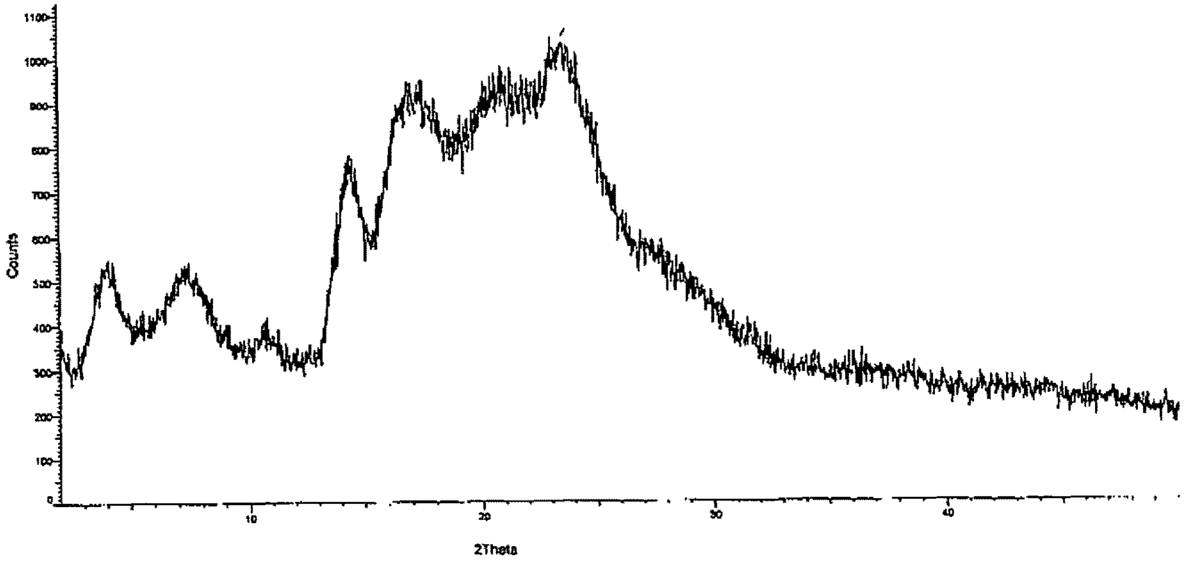
FIG. 9: Illustrates the PXRD pattern of crystalline form-S of oxalate salt of (S)-methyl-2-methoxy-5-(((1-(4-phenyl-1H-imidazol-2-yl)ethyl)amino)methyl)benzoate compound of formula-2b.

The twelfth aspect of the present invention relates to novel crystalline form-S of (S)-methyl-2-methoxy-5-(((1-(4-phenyl-1H-imidazol-2-yl)ethyl)amino)methyl)benzoate oxalate salt compound of formula-2b characterized by its X-ray powder diffractogram as illustrated in FIG. 9.

Further embodiment of the present invention provides a process for the preparation of crystalline form-S of (S)-methyl-2-methoxy-5-(((1-(4-phenyl-1H-imidazol-2-yl)ethyl)amino) methyl)benzoate oxalate salt compound of formula-4b comprising of the following steps:

a) Adding isopropanol to (S)-methyl-2-methoxy-5-(((1-(4-phenyl-1H-imidazol-2-yl) ethyl)amino)methyl)benzoate compound of formula-2.

b) adding oxalic acid to the reaction mixture.

c) stirring the reaction mixture at 25-30° C.

d) filtering the precipitated solid to get the crystalline form-S of (S)-methyl-2-methoxy-5-(((1-(4-phenyl-1H-imidazol-2-yl)ethyl)amino)methyl)benzoate oxalate salt compound of formula-2b.

Further, in another embodiment of the present invention the acid addition salts of (S)-methyl-2-methoxy-5-(((1-(4-phenyl-1H-imidazol-2-yl)ethyl)amino)methyl)benzoate compound of formula-2 can be converted into highly pure (S)-methyl-2-methoxy-5-(((1-(4-phenyl-1H-imidazol-2-yl)ethyl)amino)methyl)benzoate compound of formula-2 by treating with a suitable base.

According to the prior known process, (S)-methyl-2-methoxy-5-(((1-(4-phenyl-1H-imidazol-2-yl)ethyl)amino) methyl)benzoate compound of formula-2 is obtained as residue with low yield and high impurities.

Utilizing such a low quality compound of formula-2 will carry over impurities and leads to decrease the yield and purity of the subsequent steps as well as the final compound of formula-1.

In order to reduce the level of the impurities, it is necessary to carry out a number of purifications at this stage. Generally, purification leads to loss of material, generation of lot of spent solvents and solid waste which are difficult to dispose which may lead to the pollution of the environment. Further, the said process increases the cost of the production and which is not recommended for commercial scale-up.

In order to overcome the aforementioned problems, inventors of the present invention have surprisingly found that by the conversion of (S)-methyl-2-methoxy-5-(((1-(4-phenyl-1H-imidazol-2-yl)ethyl)amino)methyl)benzoate compound of formula-2 into its acid addition salts compound of formula-2 and then conversion of the acid addition salts of compound of formula-2 into free base by treating with a suitable base to provide pure (S)-methyl-2-methoxy-5-(((1-(4-phenyl-1H-imidazol-2-yl)ethyl)amino)methyl) benzoate compound of formula-2 with high purity.

The thirteenth aspect of the present invention provides novel intermediate compounds represented by the following structural formula:

Formula-12

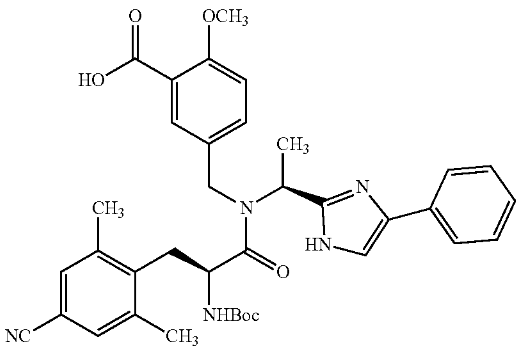

Formula-13

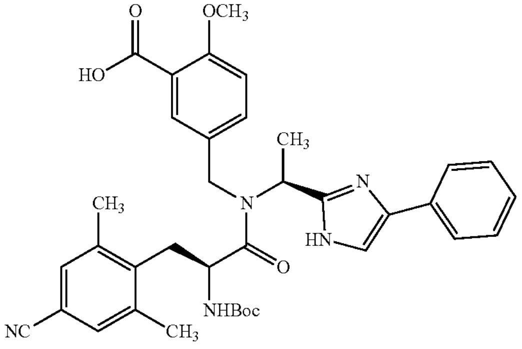

-continued

Formula-14

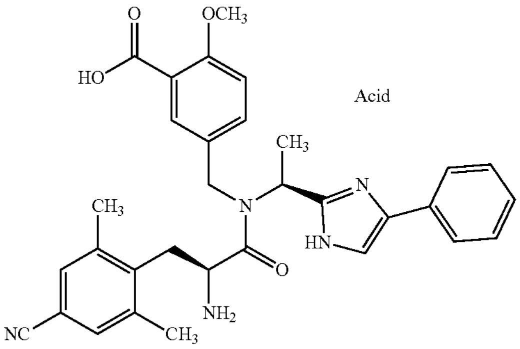

Acid

Formula-15

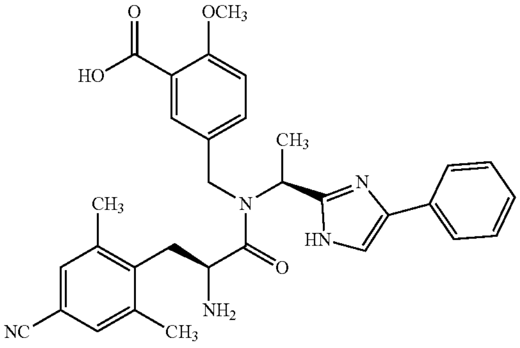

The novel compounds of formula-12, 13, 14 and 15 are useful in the preparation of compound of formula-1.

The fourteenth aspect of the present invention provide an improved process for the preparation of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1.

The process of the present invention is schematically represented as below:

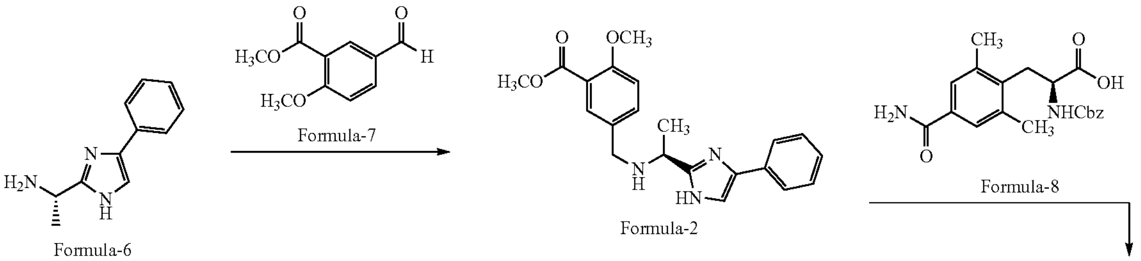

Formula-6

Formula-7

Formula-2

Formula-8

-continued

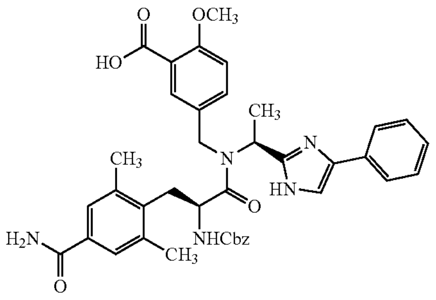

Formula-10

Hydrolysis

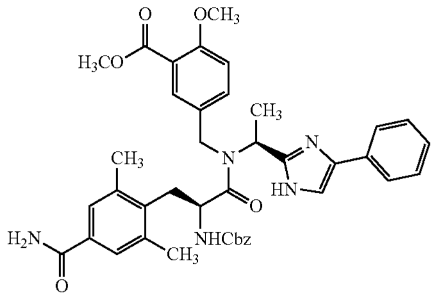

Formula-9

Reduction

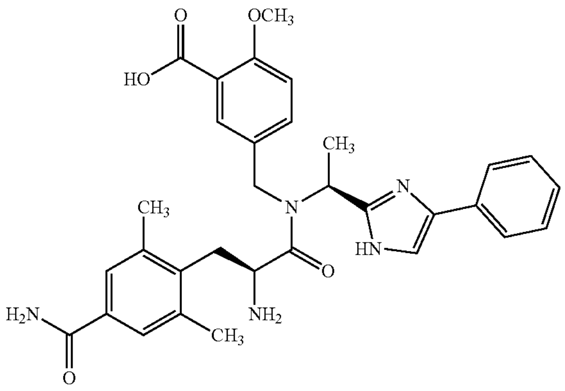

Formula-1

2a = Maleate
2b = Oxalate

The fifteenth aspect of the present invention provides novel process for the preparation of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1.

The process of the present invention is schematically represented as below:

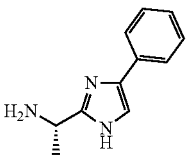

Formula-6

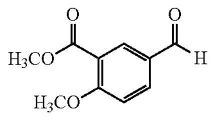

Formula-7

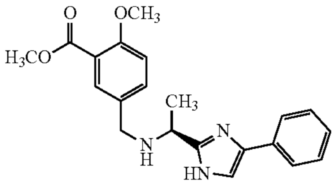

Formula-2

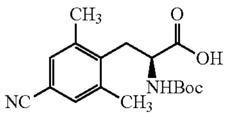

Formula-11

Condensation

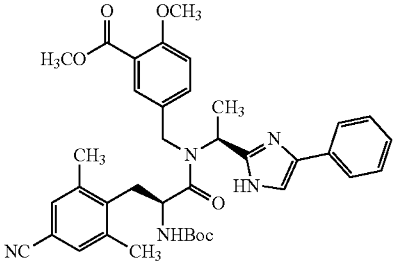

Formula-12

Hydrolysis

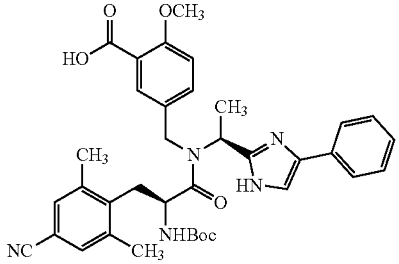

Formula-13

Deprotection

-continued

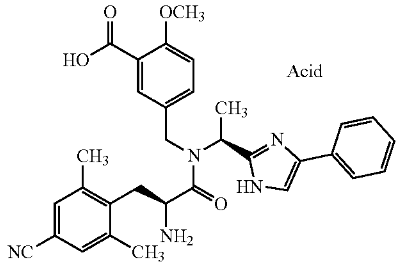

Formula-14

Base

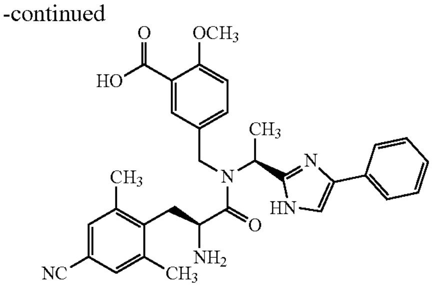

Formula-15

Hydrolysis

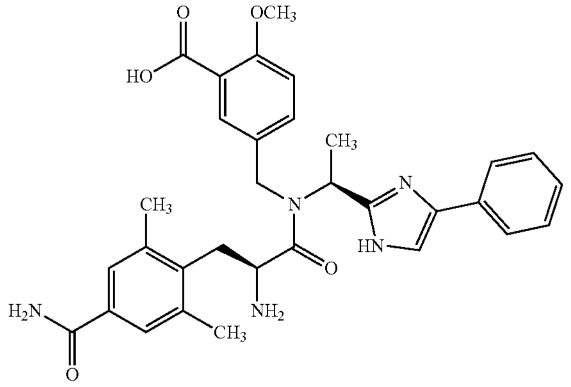

Formula-1

2a = Maleate
2b = Oxalate

Figure 10:
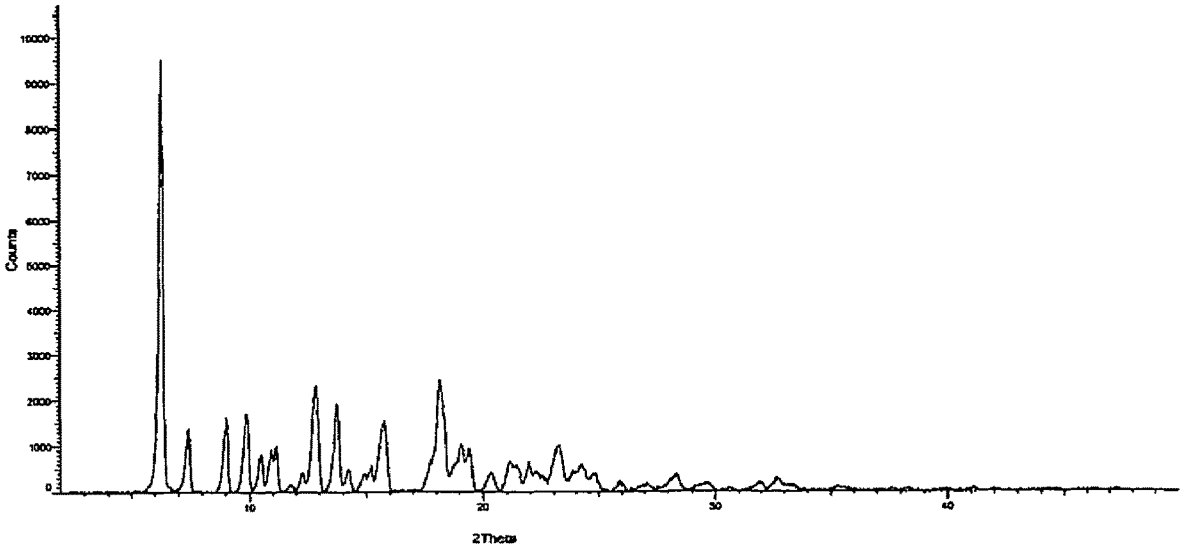
FIG. 10: Illustrates the PXRD pattern of crystalline form-N1 of 5-[[[(2S)-2-amino-3-[4-(aminocarbonyl)-2,6-dimethylphenyl]-1-oxopropyl][(1S)-1-(4-phenyl-1H-imidazol-2-yl) ethyl]amino]methyl]-2-methoxybenzoic acid compound of formula-1.

The sixteenth aspect of the present invention provides crystalline form-N1 of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1, characterized by its powder x-ray diffraction pattern having peaks at 6.3, 7.4, 9.0, 9.8, 10.4, 10.9, 11.1, 11.7, 12.2, 12.8, 13.7, 14.2, 14.9, 15.1, 15.7, 17.7, 18.1, 19.0, 19.4, 20.3, 21.1, 21.3, 21.9, 22.2, 22.5, 23.1, 23.8, 24.2, 24.8, 25.9, 27.1, 28.3, 31.9 and 32.6±0.2 degrees two theta and P-XRD pattern as depicted in FIG. 10.

In an embodiment of the present invention provides a process for the preparation of crystalline form-N1 of 5-[[[(2S)-2-amino-3-[4-(aminocarbonyl)-2,6-dimethylphenyl]-1-oxo propyl][(1S)-1-(4-phenyl-1H-imidazol-2-yl) ethyl]amino]methyl]-2-methoxybenzoic acid compound of formula-1, comprising of:

a) Adding a suitable solvent to 5-[[[(2S)-2-amino-3-[4-(aminocarbonyl)-2,6-dimethyl phenyl]-1-oxopropyl][(1S)-1-(4-phenyl-1H-imidazol-2-yl)ethyl]amino]methyl]-2-methoxybenzoic acid compound of formula-1,
b) heating the reaction mixture to a suitable temperature,
c) stirring the reaction mixture,
d) cooling the reaction mixture,
e) filtering the solid to get the crystalline form-N1 of 5-[[[(2S)-2-amino-3-[4-(amino carbonyl)-2,6-dimethylphenyl]-1-oxopropyl][(1S)-1-(4-phenyl-1H-imidazol-2-yl) ethyl]amino]methyl]-2-methoxybenzoic acid.

Wherein, in step-a) the suitable solvent is selected from alcohol solvents, preferably isopropanol; in step-b) the suitable temperature is ranging from 25° C. to the reflux temperature of the solvent used in the reaction.

The preferred embodiment of the present invention provides a process for the preparation of crystalline form-N1 of 5-[[[(2S)-2-amino-3-[4-(aminocarbonyl)-2,6-dimethyl phenyl]-1-oxopropyl][(1S)-1-(4-phenyl-1H-imidazol-2-yl) ethyl]amino]methyl]-2-methoxy benzoic acid compound of formula-1, comprising of:

a) Adding isopropanol to 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxy benzoic acid compound of formula-1,
b) heating the reaction mixture to 60-65° C.,
c) stirring the reaction mixture,
d) cooling the reaction mixture,
e) filtering the solid to get the crystalline form-N1 of 5-[[[(2S)-2-amino-3-[4-(amino carbonyl)-2,6-dimethylphenyl]-1-oxopropyl][(1S)-1-(4-phenyl-1H-imidazol-2-yl) ethyl]amino]methyl]-2-methoxybenzoic acid.

Figure 11:
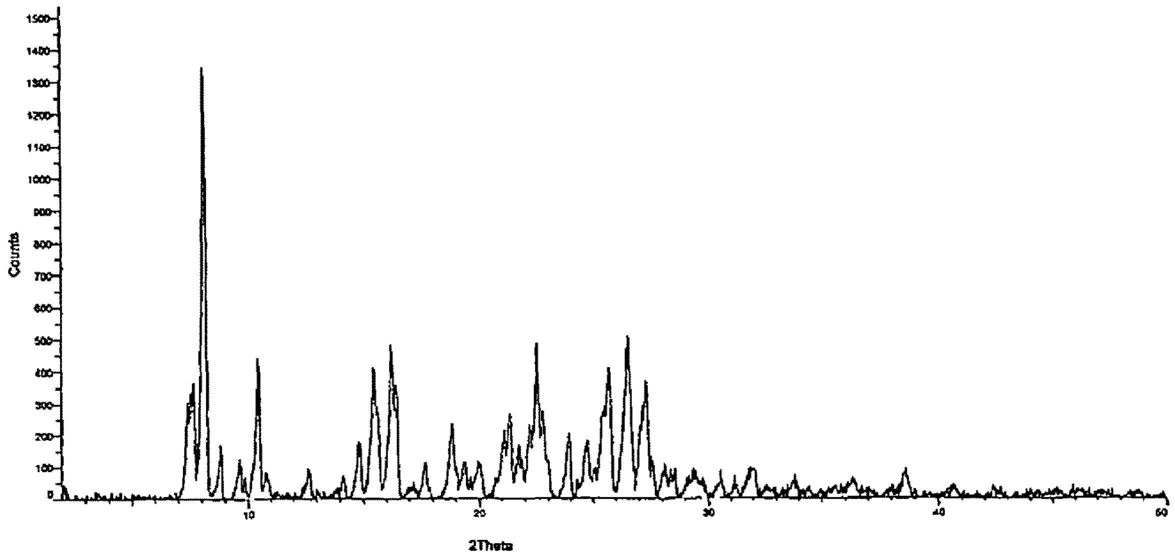
FIG. 11: Illustrates the PXRD pattern of crystalline form-N2 of 5-[[[(2S)-2-amino-3-[4-(aminocarbonyl)-2,6-dimethylphenyl]-1-oxopropyl][(1S)-1-(4-phenyl-1H-imidazol-2-yl) ethyl]amino]methyl]-2-methoxybenzoic acid compound of formula-1.

The seventeenth aspect of the present invention provides crystalline form-N2 of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1, characterized by its powder x-ray diffraction pattern having peaks at 7.4, 7.6, 8.1, 8.7, 9.6, 9.8, 10.4, 10.7, 12.6, 14.1, 14.8, 15.4, 15.5, 16.1, 16.4, 17.6, 18.8, 19.3, 19.9, 21.2, 21.3, 21.7, 22.3, 22.5, 22.7, 23.8, 24.7, 25.0, 25.4, 25.6, 26.5, 27.2, 28.0, 28.4, 29.1, 29.3, 31.9, 36.3 and 38.5±0.2 degrees two theta and P-XRD pattern as depicted in FIG. 11.

In an embodiment of the present invention provides a process for the preparation of crystalline form-N2 of 5-[[[(2S)-2-amino-3-[4-(aminocarbonyl)-2,6-dimethylphenyl]-1-oxo propyl][(1S)-1-(4-phenyl-1H-imidazol-2-yl) ethyl]amino]methyl]-2-methoxybenzoic acid compound of formula-1, comprising of:

a) Adding a suitable solvent to 5-[[[(2S)-2-amino-3-[4-(aminocarbonyl)-2,6-dimethyl phenyl]-1-oxopropyl]

[(1S)-1-(4-phenyl-1H-imidazol-2-yl)ethyl]amino]methyl]-2-methoxybenzoic acid compound of formula-1, b) heating the reaction mixture to a suitable temperature, c) adding a suitable solvent, d) stirring the reaction mixture, e) cooling the reaction mixture, f) filtering the precipitated solid to get the crystalline form-N2 of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid.

Wherein, in step-a) the suitable solvent is selected from alkyl formate; preferably ethyl formate; in step-b) the suitable temperature is ranging from 25° C. to the reflux temperature of the solvent used in the reaction;

in step-c) the suitable solvent is selected from ketone solvents, ester solvents, chloro solvents, ether solvents, hydrocarbon solvents and polar solvent like water or mixture thereof.

The preferred embodiment of the present invention provides a process for the preparation of crystalline form-N2 of 5-[[[(2S)-2-amino-3-[4-(aminocarbonyl)-2,6-dimethyl phenyl]-1-oxopropyl][(1S)-1-(4-phenyl -1H-imidazol-2-yl) ethyl]amino]methyl]-2-methoxy benzoic acid compound of formula-1, comprising of:

a) Adding ethyl formate to 5-[[[(2S)-2-amino-3-[4-(aminocarbonyl)-2,6-dimethyl phenyl]-1-oxopropyl][(1S)-1-(4-phenyl-1H-imidazol-2-yl)ethyl]amino]methyl]-2-methoxybenzoic acid compound of formula-1, b) heating the reaction mixture to 60-65° C., c) adding a mixture of ethyl acetate and methyl tert-butyl ether, d) stirring the reaction mixture, e) cooling the reaction mixture, f) filtering the precipitated solid to get the crystalline form-N2 of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid.

Figure 12:
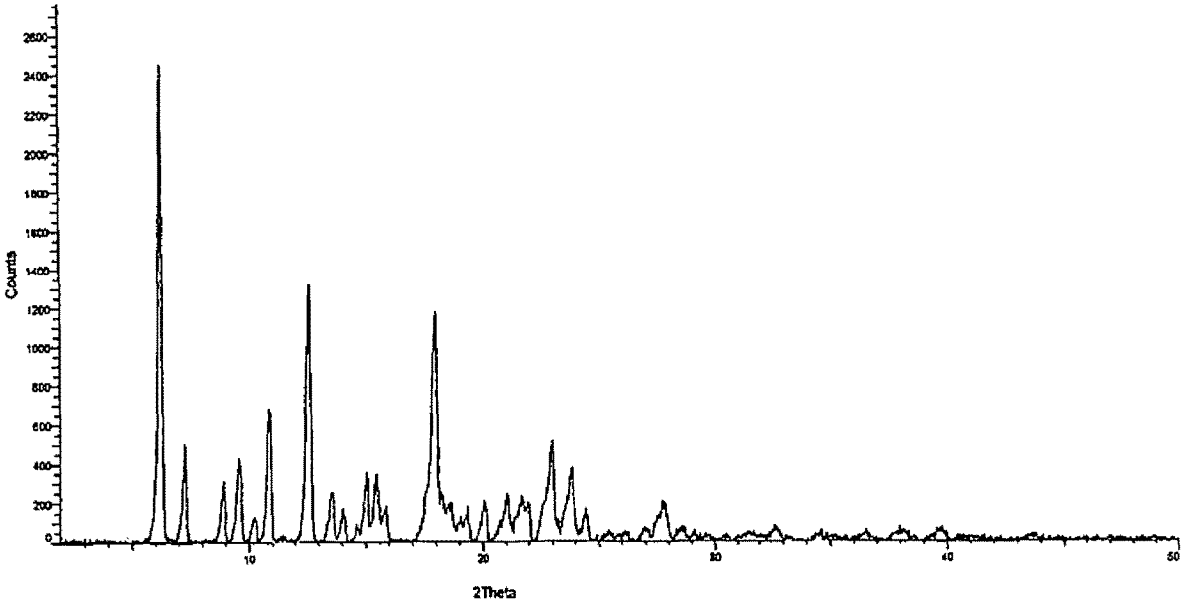
FIG. 12: Illustrates the PXRD pattern of crystalline form-N3 of 5-[[[(2S)-2-amino-3-[4-(aminocarbonyl)-2,6-dimethylphenyl]-1-oxopropyl][(1S)-1-(4-phenyl-1H-imidazol-2-yl) ethyl]amino]methyl]-2-methoxybenzoic acid compound of formula-1.

The eighteenth aspect of the present invention provides crystalline form-N3 of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1, characterized by its powder x-ray diffraction pattern having peaks at 6.2, 7.2, 8.9, 9.6, 10.2, 10.8, 12.6, 13.5, 13.9, 14.0, 14.6, 15.0, 15.4, 15.8, 17.9, 18.1, 19.0, 19.3, 20.0, 21.0, 21.6, 21.9, 22.9, 23.8, 24.4 and 27.7±0.2 degrees two theta and P-XRD pattern as depicted in FIG. 12.

In an embodiment of the present invention provides a process for the preparation of crystalline form-N3 of 5-[[[(2S)-2-amino-3-[4-(aminocarbonyl)-2,6-dimethylphenyl]-1-oxo propyl][(1S)-1-(4-phenyl-1H-imidazol-2-yl) ethyl]amino]methyl]-2-methoxybenzoic acid compound of formula-1, comprising of:

a) Adding a suitable solvent to 5-[[[(2S)-2-amino-3-[4-(aminocarbonyl)-2,6-dimethyl phenyl]-1-oxopropyl][(1S)-1-(4-phenyl-1H-imidazol-2-yl)ethyl]amino]methyl]-2-methoxybenzoic acid compound of formula-1, b) heating the reaction mixture to a suitable temperature, c) stirring the reaction mixture, d) cooling the reaction mixture, e) filtering the precipitated solid to get the crystalline form-N3 of 5-[[[(2S)-2-amino-3-[4-(aminocarbonyl)-2,6-dimethylphenyl]-1-oxopropyl][(1S)-1-(4-phenyl-1H-imidazol-2-yl) ethyl]amino]methyl]-2-methoxybenzoic acid.

Wherein, in step-a) the suitable solvent is selected from ketone solvents, preferably methyl isobutyl ketone;

in step-b) the suitable temperature is ranging from 25° C. to the reflux temperature of the solvent used in the reaction;

The preferred embodiment of the present invention provides a process for the preparation of crystalline form-N3 of 5-[[[(2S)-2-amino-3-[4-(aminocarbonyl)-2,6-dimethyl phenyl]-1-oxopropyl][(1S)-1-(4-phenyl-1H-imidazol-2-yl) ethyl]amino]methyl]-2-methoxy benzoic acid compound of formula-1, comprising of:

a) Adding methyl isobutyl ketone to 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1, b) heating the reaction mixture to 60-65° C., c) stirring the reaction mixture, d) cooling the reaction mixture, e) filtering the precipitated solid to get the crystalline form-N3 of 5-[[[(2S)-2-amino-3-[4-(aminocarbonyl)-2,6-dimethylphenyl]-1-oxopropyl][(1S)-1-(4-phenyl-1H-imidazol-2-yl) ethyl]amino]methyl]-2-methoxybenzoic acid.

The nineteenth aspect of the present invention provides amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with one or more pharmaceutical acceptable carrier.

Wherein, the term pharmaceutical acceptable carrier is preferably a polymeric carrier, and more preferably at least one from the group consisting of starches, modified starches, cellulose, methyl cellulose (MC), Microcrystalline cellulose (MCC), ethyl cellulose (EC), hydroxyethyl cellulose (HEC), hydroxypropyl cellulose (HPC), hydroxypropylmethyl cellulose (HPMC), hydroxypropylmethylcellulose acetate succinate (HPMC AS), polycarbophil, polyethylene glycol (PEG), polyethylene oxides, polyoxyalkylene derivatives, polymethacrylates, polyvinyl pyrrolidone (PVP), PVP K-30, polyvinyl acetate (PVAc), PVP vinylacetate-copolymer (PVP-VA), Kollidon VA 64 (vinylpyrrolidone-vinyl acetate copolymer), lactose, sorbitol, mannitol, maltitol, saccharose, isomalt, cyclodextrins such as cc-cyclodextrins, β-cyclodextrins, γ-cyclodextrins, hydroxyl-propyl-cyclodextrins, hydroxyl propyl-cyclodextrin, sodium carboxymethyl cellulose cross-linked polyacrylic acid (carbipol), or a mixture thereof.

In general, the term "solid dispersion" refers to a system in a solid state comprising at least two components, wherein one component is dispersed throughout the other component or components.

The term "amorphous solid dispersion" as used herein, refers to solid dispersion which is substantially amorphous, that is, at least 80%, preferably at least 90%, most preferably at least 95%, is in amorphous form as determined by powder x-ray diffraction pattern.

Figure 13:
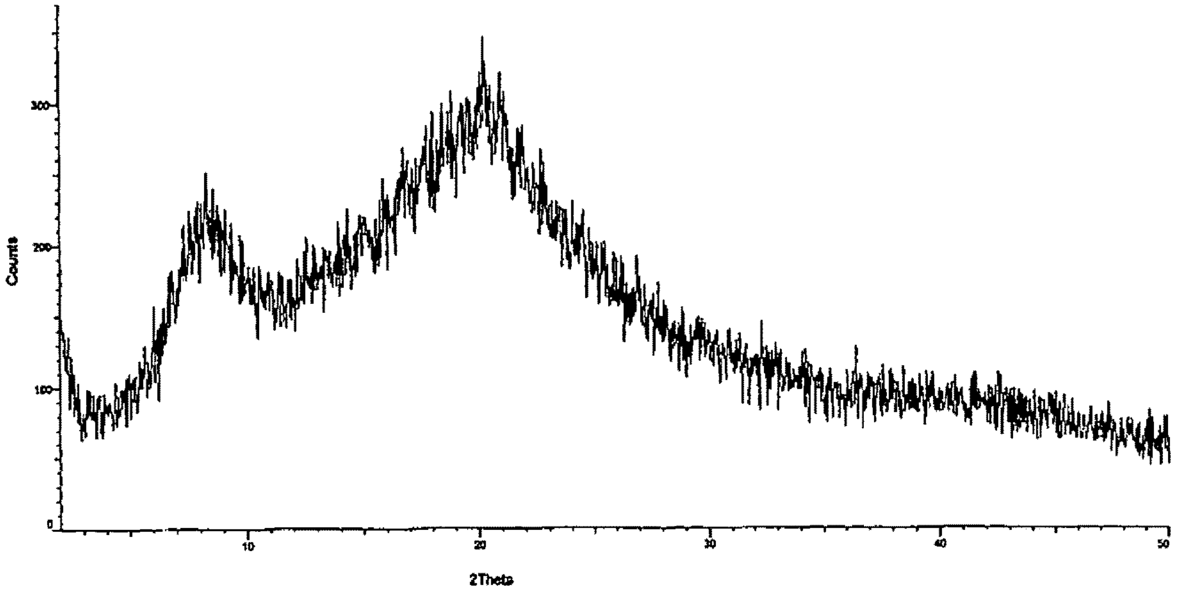
FIG. 13: Illustrates the PXRD pattern of amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl) ethyl]amino]methyl]-2-methoxybenzoic acid in combination with HPC.

In an embodiment of the present invention provides amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with HPC and the P-XRD pattern is depicted in FIG. 13.

The another embodiment of the present invention provides amorphous solid dispersion of 5-[[[(2S)-2-amino-3-

Figure 14:
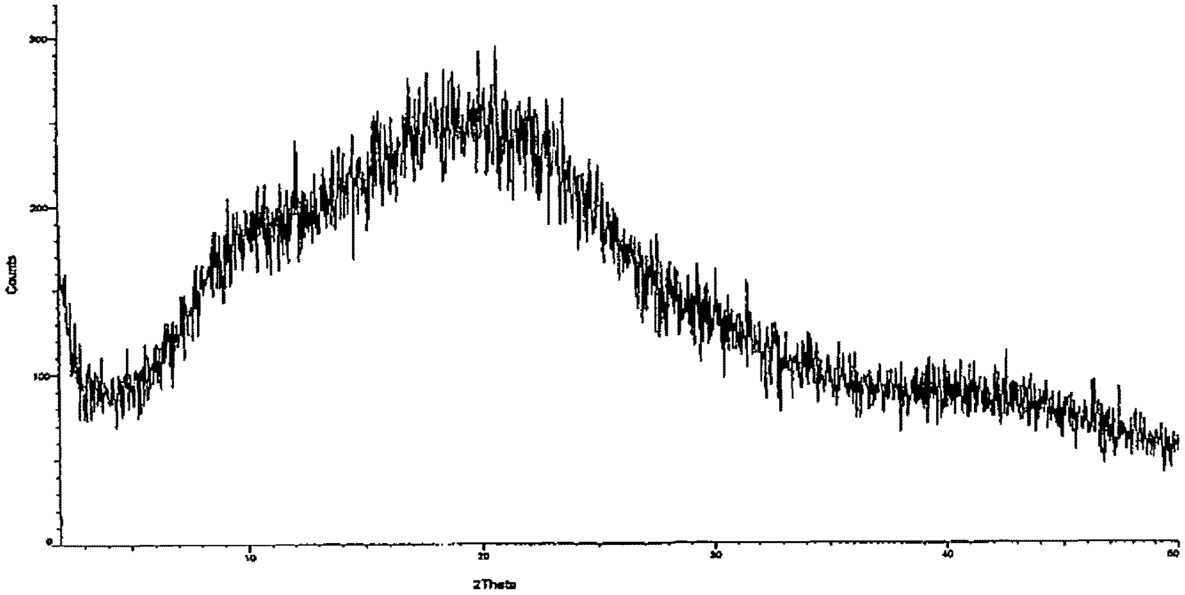

[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with HPMC AS and the P-XRD pattern is depicted in FIG. 14.

Figure 15:
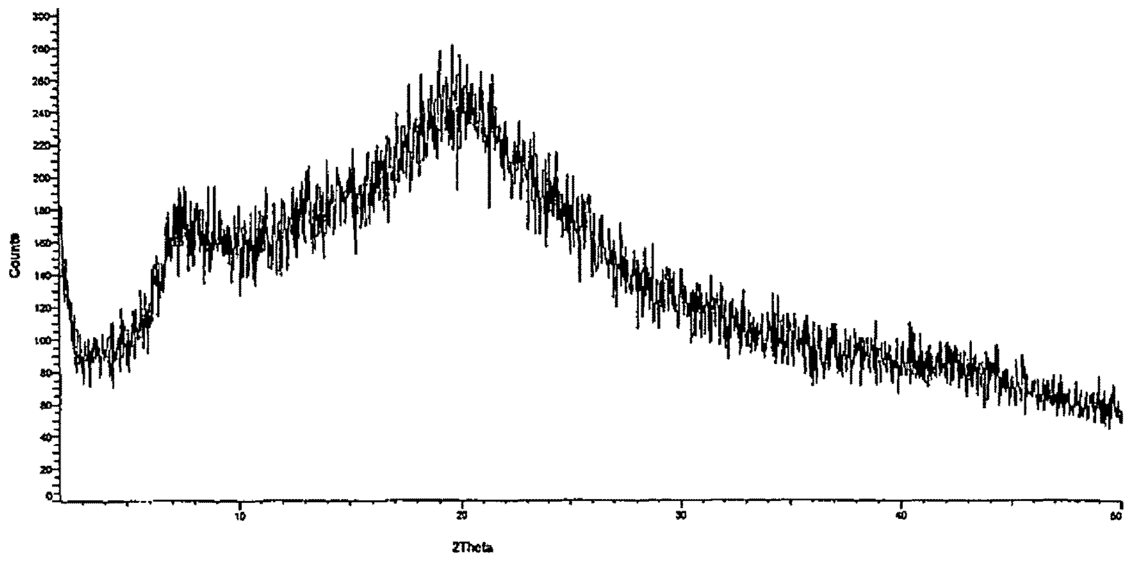
FIG. 15: Illustrates the PXRD pattern of amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl) ethyl]amino]methyl]-2-methoxybenzoic acid in combination with HPMC.

The another embodiment of the present invention provides amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with HPMC and the P-XRD pattern is depicted in FIG. 15.

Figure 16:
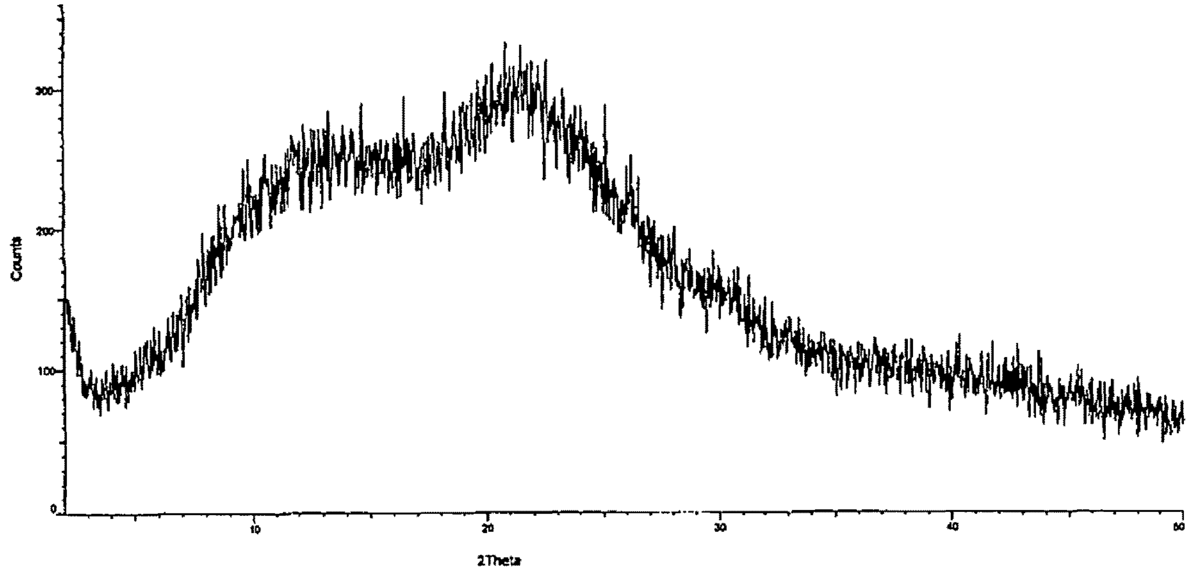
FIG. 16: Illustrates the PXRD pattern of amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl) ethyl]amino]methyl]-2-methoxybenzoic acid in combination with PVP K-30.

The another embodiment of the present invention provides amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with PVP K-30 and the P-XRD pattern is depicted in FIG. 16.

In another embodiment of the present invention provides process for the preparation of amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with one or more pharmaceutical acceptable carrier, comprising of:

a) Dissolving a mixture of 5-[[[(2S)-2-amino-3-[4-(aminocarbonyl)-2,6-dimethyl phenyl]-1-oxopropyl][(1S)-1-(4-phenyl-1H-imidazol-2-yl)ethyl]amino]methyl]-2-methoxybenzoic acid and one or more pharmaceutical acceptable carrier in a suitable solvent, b) stirring the reaction mixture, c) isolating amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with one or more pharmaceutical acceptable carrier.

Wherein, in step-a) the suitable solvent is selected from alcohol solvents, ketone solvents, ester solvents, hydrocarbon solvents, ether solvents, polar aprotic solvents, nitrile solvents and polar solvents like water or mixture thereof and suitable pharmaceutical acceptable carrier is same as defined in the nineteenth aspect of the present invention.

The preferred embodiment of the present invention provides a process for the preparation of amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with HPC, comprising of:

a) Dissolving a mixture of 5-[[[(2S)-2-amino-3-[4-(aminocarbonyl)-2,6-dimethyl phenyl]-1-oxopropyl][(1S)-1-(4-phenyl-1H-imidazol-2-yl)ethyl]amino]methyl]-2-methoxybenzoic acid and HPC in methanol, b) stirring the reaction mixture, c) isolating amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino] methyl]-2-methoxybenzoic acid compound of formula-1 in combination with HPC.

In another preferred embodiment of the present invention provides a process for the preparation of amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with HPMC, comprising of:

a) Dissolving a mixture of 5-[[[(2S)-2-amino-3-[4-(aminocarbonyl)-2,6-dimethyl phenyl]-1-oxopropyl][(1S)-1-(4-phenyl-1H-imidazol-2-yl)ethyl]amino]methyl]-2-methoxybenzoic acid and HPMC in methanol, b) stirring the reaction mixture, c) isolating amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with HPMC.

In another preferred embodiment of the present invention provides a process for the preparation of amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with PVP K-30, comprising of a) Dissolving a mixture of 5-[[[(2S)-2-amino-3-[4-(aminocarbonyl)-2,6-dimethyl phenyl]-1-oxopropyl][(1S)-1-(4-phenyl-1H-imidazol-2-yl)ethyl]amino]methyl]-2-methoxybenzoic acid and PVP K-30 in methanol, b) stirring the reaction mixture, c) isolating amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino] methyl]-2-methoxybenzoic acid compound of formula-1 in combination with PVP K-30.

In another preferred embodiment of the present invention provides a process for the preparation of amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 in combination with HPMC AS, comprising of:

a) Dissolving a mixture of 5-[[[(2S)-2-amino-3-[4-(aminocarbonyl)-2,6-dimethyl phenyl]-1-oxopropyl][(1S)-1-(4-phenyl-1H-imidazol-2-yl)ethyl]amino]methyl]-2-methoxybenzoic acid and HPMC AS in methanol, b) stirring the reaction mixture, c) isolating amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino] methyl]-2-methoxybenzoic acid compound of formula-1 in combination with HPMC AS.

The amorphous solid dispersion of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid obtained according to the present invention can be isolated using a rotational distillation device such as a Buchi Rota vapor, vacuum drying, spray drying, spray granulating, freeze drying and spray-freeze drying, agitated thin film drying (ATFD) or melt extrusion or freeze drying (lyophilization) or by any other suitable techniques.

In the present invention, the composition of the solid dispersion containing of a mole ratio of the amount of the 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 to the amount of the pharmaceutical acceptable carrier is ranging from about 1:0.5 to 1:10 by weight.

5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 produced by the present invention can be further micronized or milled in a conventional techniques to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

The present inventors repeated the process of the preparation of compound of formula-1 according to example-1 of U.S. Pat. No. 7,994,206 B2 and characterized the obtained solid with P-XRD pattern and which is given in FIG. 18.

5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 used for the preparation of crystalline forms and amorphous forms of the present invention is prepared according to the process of the present invention or any of the process known in the art.

5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 obtained according to the present invention is having purity greater than 99.96% as measured by HPLC.

5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 obtained according to the present invention is having particle size distribution $D_{90}<100$ μm.

5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid compound of formula-1 produced by the present invention can be further micronized or milled in a conventional techniques to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

The invention also encompasses pharmaceutical compositions comprising compound of formula-1 or salts thereof of the present invention. As used herein, the term "pharmaceutical compositions" or "pharmaceutical formulations" include tablets, pills, powders, liquids, suspensions, emulsions, granules, capsules, suppositories, or injection preparations.

P-XRD Method of Analysis:

PXRD analysis of compounds produced by the present invention were carried out using BRUKER D8 ADVANCE/AXS X-Ray diffractometer using Cu Kα radiation of wavelength 1.5406 A° and continuous scan speed of 0.03°/min.

PSD Method of Analysis:

Particle size distribution (PSD) analysis was performed using Malvern Mastersizer 2000 instrument.

The process of the present invention can be represented schematically as follows:

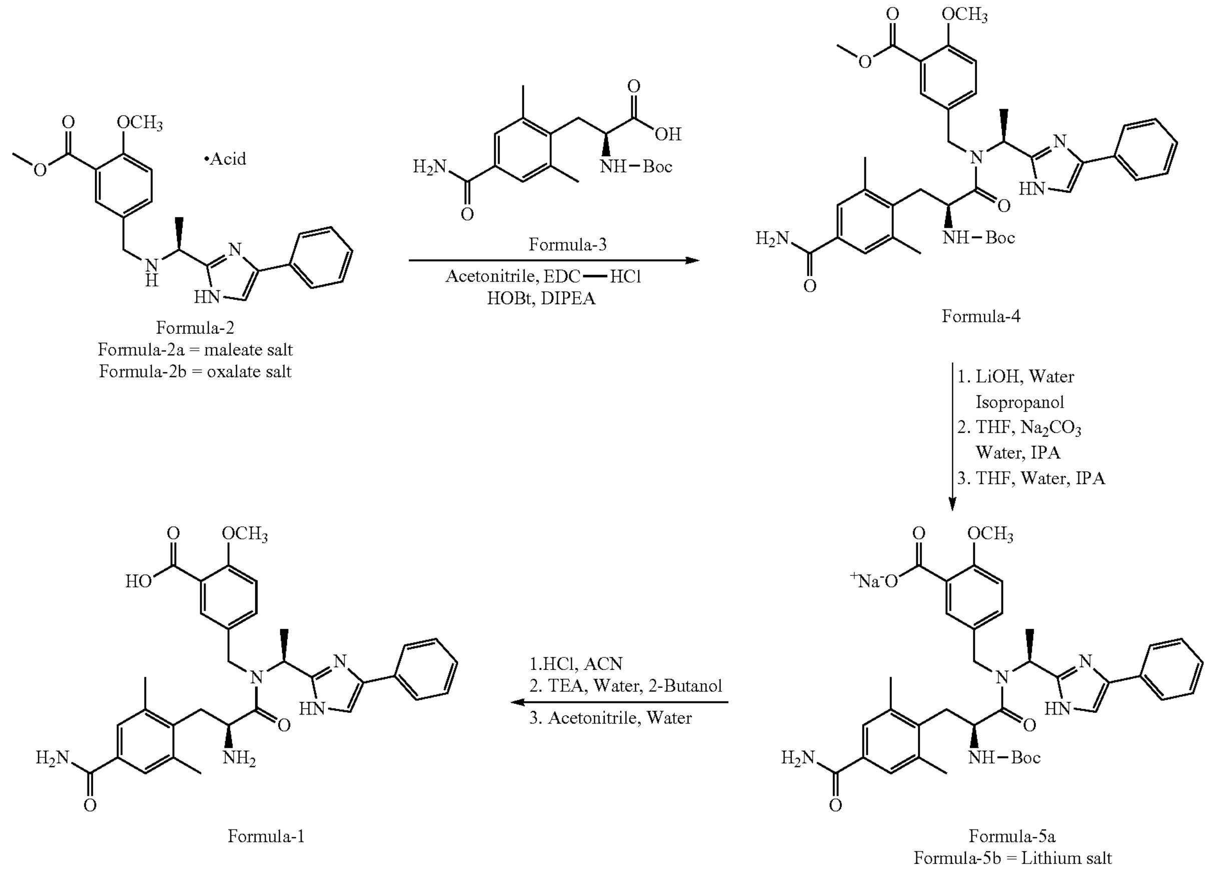

The process described in the present invention was demonstrated in examples illustrated below. These examples are provided as illustration only and therefore should not be construed as limitation of the scope of the invention.

EXAMPLES

Example-1

Preparation of methyl-5-(((S)-2-((tert-butoxycarbonyl)amino)-3-(4-carbamoyl-2,6-dimethylphenyl)-N—((S)-1-(4-phenyl-1H-imidazol-2-yl)ethyl)propanamido)methyl)-2-methoxybenzoate: (Formula-4)

Hydroxybenzotriazole (20.0 gms) and N-(3-dimethylaminopropyl)-N'-ethyl carbodiimide hydrochloride (56.8 gms) were added to a mixture of acetonitrile (500 ml) and (S)-2-((tert-butoxycarbonyl)amino)-3-(4-carbamoyl-2,6-dimethylphenyl)propanoic acid (100 gms) compound of formula-3 at 10-15° C. and stirred for 30 minutes at the same temperature. (S)-methyl-2-methoxy-5-(((1-(4-phenyl-1H-imidazol-2-yl)ethyl)amino)methyl)benzoate maleate (142.8 gms) compound of formula-2a was added to the reaction mixture at 10-15° C. Diisopropylethylamine (76.8 gms) was slowly added to the reaction mixture at 10-15° C. Raised the temperature of the reaction mixture to 25-30° C. and stirred for 90 minutes at the same temperature. N-(3-dimethylaminopropyl)-N'-ethylcarbodiimide hydrochloride (28.4 gms) was added to the reaction mixture at 25-30° C. and stirred for 1 hour at the same temperature. Water (1.0 ltr) and ethyl acetate (600 ml) were added to the reaction mixture at 25-30° C. and stirred for 20 minutes at the same temperature. Both the organic and aqueous layers were separated and aqueous layer was extracted with ethyl acetate. Combined the organic layers and washed twice with aqueous sodium carbonate solution followed with hydrochloric acid solution at 25-30° C. Further, organic layer was washed with aqueous sodium chloride solution. Distilled off the solvent completely from the organic layer under reduced pressure. Isopropanol (200 ml) was added to the obtained solid at 40-45° C. Distilled off the solvent completely from the reaction mixture under reduced pressure.

Yield: 172.8 gms.

Example-2

Preparation of 5-(((S)-2-((tert-butoxycarbonyl)amino)-3-(4-carbamoyl-2,6-dimethylphenyl)-N—((S)-1-(4-phenyl-1H-imidazol-2-yl)ethyl)propanamido)methyl)-2-methoxy benzoate lithium salt: (Formula-5b)

Aqueous lithium hydroxide solution was slowly added to a mixture of methyl-5-(((S)-2-((tert-butoxycarbonyl)amino)-3-(4-carbamoyl-2,6-dimethylphenyl)-N—((S)-1-(4-phenyl-1H-imidazol-2-yl)ethyl)propanamido)methyl)-2-methoxybenzoate (172.8 gms) and isopropanol (864 ml) at 0-5° C. Raised the reaction mixture temperature to 25-30° C. and stirred for 12 hours at the same temperature. Heated the reaction mixture to 40-45° C. and stirred for 3 hours at the same temperature. Cooled the reaction mixture to 25-30° C. Isopropanol (4150 ml) was added to the reaction mixture at 25-30° C. and stirred for 45 minutes at the same temperature. Filtered the precipitated solid, washed with isopropanol and dried to get the title compound.

Yield: 145.0 gms, Purity by HPLC: 99.45%; Boc alcohol impurity: 0.13%; Boc diacid impurity: 0.13%; Boc isopropyl ester impurity: 0.18%; Boc ester impurity: 0.01%; Acid impurity: 0.01%; SMUI: 0.13%.

The P-XRD pattern of the obtained compound was depicted in FIG. 2.

Example-3

Preparation of 5-(((2S)-2-((tert-butoxycarbonyl)amino)-3-(4-carbamoyl-2,6-dimethylphenyl)-N-((1S)-1-(4-phenyl-1H-imidazol-2-yl)ethyl)propanamido)methyl)-2-methoxybenzoate sodium salt: (Formula-5a)

Tetrahydrofuran (870 ml) and water (435 ml) was added to 5-(((S)-2-((tert-butoxy carbonyl)amino)-3-(4-carbamoyl-2,6-dimethylphenyl)-N—((S)-1-(4-phenyl-1H-imidazol-2-yl) ethyl)propanamido)methyl)-2-methoxybenzoate lithium salt (145 gms) at 25-30° C. Sodium carbonate (27.3 gms) was added to the reaction mixture at 25-30° C. Heated the reaction mixture to 40-45° C. and stirred for 45 minutes at the same temperature. Cooled the reaction mixture to 25-30° C. Isopropanol (2175 ml) was added to the reaction mixture at 25-30° C. and stirred for 3 hours at the same temperature. Filtered the precipitated solid, washed with tetrahydrofuran. To the obtained solid, tetrahydrofuran (840 ml) and water (420 ml) was added at 25-30° C. Heated the reaction mixture to 40-45° C. and stirred for 45 minutes at the same temperature. Cooled the reaction mixture to 25-30° C. Isopropanol was added to the reaction mixture at 25-30° C. and stirred for 3 hours at the same temperature. Filtered the precipitated solid, washed with tetrahydrofuran and dried to get the title compound.

Yield: 130 gms; Purity by HPLC: 99.84%; Boc alcohol impurity: 0.02%; Boc diacid impurity: 0.03%; Boc isopropyl ester impurity: 0.01%; Boc ester impurity: Not detected; Acid impurity: Not detected %; SMUI: 0.1%.

The P-XRD pattern of the obtained compound was depicted in FIG. 3.

Example-4

Preparation of Crystalline Form-M of Eluxadolinc 2-butanol Solvate

Acetonitrile (200 ml) was added to 5-(((S)-2-((tert-butoxycarbonyl)amino)-3-(4-carbamoyl-2,6-dimethylphenyl)-N—((S)-1-(4-phenyl-1H-imidazol-2-yl)ethyl)propanamido)methyl)-2-methoxy benzoate sodium salt (100 gms) at 25-30° C. Cooled the reaction mixture to 0-5° C. Acetonitrile (100 ml) and hydrochloric acid solution was slowly added to the reaction mixture at 0-5° C. Raised the temperature of the reaction mixture to 20-25° C. and stirred for 4 hours at the same temperature. Water was added to the reaction mixture at 20-25° C. Cooled the reaction mixture to 0-5° C. Neutralizing the reaction mixture using triethyl amine at 0-5° C. 2-Butanol (3000 ml) was added to the reaction mixture at 0-5° C. Raised the temperature of the reaction mixture to 25-30° C. and stirred for 6 hours at the same temperature. Cooled the reaction mixture to 0-5° C. and stirred for 2 hours at the same temperature. Filtered the precipitated solid, washed with 2-butanol and dried to get the title compound. Yield: 76.5 gms; M.R: 185-190° C.; 2-Butanol content: 13.35%.

Purity by HPLC: 99.92%; Diacid impurity: 0.06%; Amide alcohol impurity: Not detected; Isopropyl ester impurity: Not detected; Boc ester impurity: 0.02%; HIUI: 0.02%; Diastereomer impurity: Not detected. Chiral purity by HPLC: 99.97%; Enantiomer impurity: 0.03%; The P-XRD pattern of the obtained compound was depicted in FIG. 1.

Example-5

Preparation of Amorphous Form of Eluxadoline

A mixture of 5-(((S)-2-amino-3-(4-carbamoyl-2,6-dimethylphenyl)-N—((S)-1-(4-phenyl-1H-imidazol-2-yl)ethyl) propanamido)methyl)-2-methoxy benzoic acid 2-butanol solvate (100 gms), acetonitrile (150 ml) and water (150 ml) was stirred for 10 minutes at 25-30° C. Heated the reaction mixture to 40-45° C. and stirred for 15 minutes at the same temperature. Filtered the reaction mixture through hyflow bed and washed with a mixture of acetonitrile and water. The filtrate was added to pre-cooled water at 0-5° C. and stirred for 2 hours at the same temperature. Filtered the precipitated solid, washed with chilled water and dried to get the title compound. Yield: 70.0 gms; M.R: 180-186° C.; Water content: 5.17% w/w.

Figure 17:
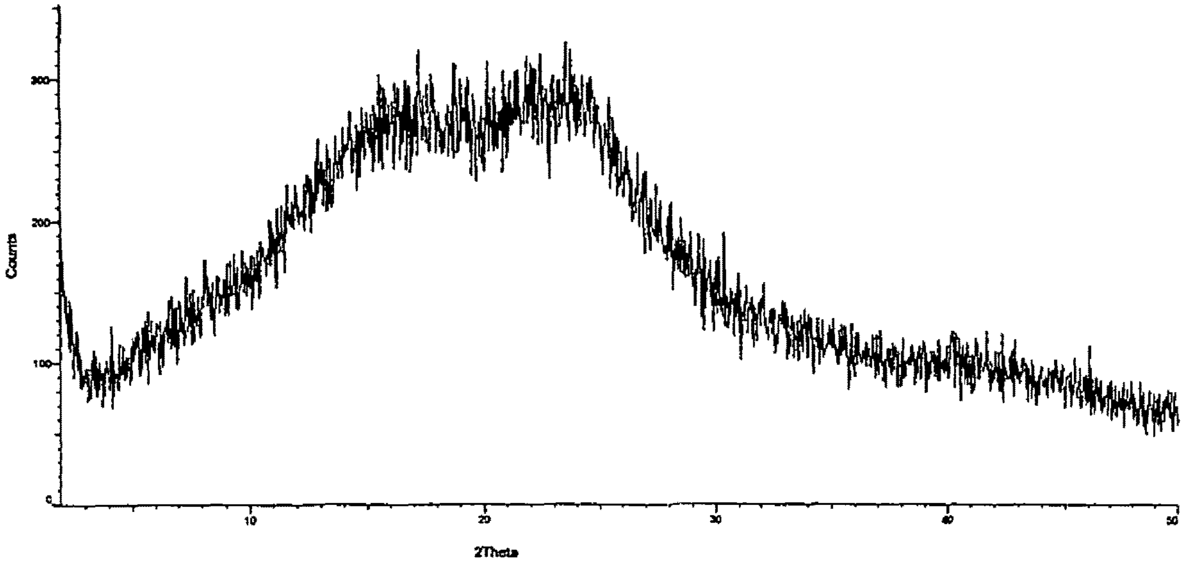
FIG. 17: Illustrates the PXRD pattern of amorphous of 5-[[[(2S)-2-amino-3-[4-(amino carbonyl)-2,6-dimethylphenyl]-1-oxopropyl][(1S)-1-(4-phenyl-1H-imidazol-2-yl) ethyl]amino]methyl]-2-methoxybenzoic acid.

Purity by HPLC: 99.95%; Diacid impurity: 0.07%; Alcohol impurity: 0.01%; Isopropyl ester impurity: 0.02%; Boc ester impurity: 0.01%; HIUI: 0.07%. Chiral purity by HPLC: 99.98%; Enantiomer impurity: 0.02%; The P-XRD of the obtained compound is depicted in FIG. 17.

Example-6

Preparation of 5-(((S)-2-((tert-butoxycarbonyl) amino)-3-(4-carbamoyl-2,6-dimethylphenyl)-N—((S)-1-(4-phenyl-1H-imidazol-2-yl)ethyl)propanamido)methyl)-2-methoxybenzoate lithium salt: (Formula-5b)

Aqueous lithium hydroxide solution was slowly added to a mixture of methyl-5-(((S)-2-((tert-butoxycarbonyl) amino)-3-(4-carbamoyl-2,6-dimethylphenyl)-N—((S)-1-(4-phenyl-1H-imidazol-2-yl)ethyl )propanamido)methyl)-2-methoxybenzoate (172.8 gms) and isopropanol (864 ml) at 0-5° C. Raised the reaction mixture temperature to 25-30° C. and stirred for 12 hours at the same temperature. Heated the reaction mixture to 40-45° C. and stirred for 3 hours at the same temperature. Cooled the reaction mixture to 25-30° C. Isopropanol (4150 ml) was added to the reaction mixture at 25-30° C. and stirred for 45 minutes at the same temperature. Filtered the precipitated solid, washed with isopropanol and dried to get the title compound.

Yield: 145.0 gms; Purity by HPLC: 99.45%; Boc alcohol impurity: 0.13%; Boc diacid impurity: 0.13%; Boc isopropyl ester impurity: 0.18%; Boc ester impurity: 0.01%; Acid impurity: 0.01%; SMUI: 0.13%.

Example-7

Preparation of Crystalline Form-S3 of Eluxadoline 2-butanol Solvate: (Formula-1)

Acetonitrile (600 ml) and hydrochloric acid solution (600 ml) were added to 5-(((S)-2-((tert-butoxycarbonyl)amino)-3-(4-carbamoyl-2,6-dimethylphenyl)-N—((S)-1-(4-phenyl-1H-imidazol-2-yl)ethyl)propanamido)methyl)-2-methoxy benzoate lithium salt (200 gms) at 10-15° C. and stirred for 20 minutes at the same temperature. Raised the temperature of the reaction mixture to 25-30° C. and stirred for 4 hours at the same temperature. Water (600 ml) and 2-butanol (300 ml) were added to the reaction mixture at 25-30° C. and stirred for 15 minutes at the same temperature. Reaction mixture was neutralized by using triethylamine (750 ml) at 25-30° C. and stirred for 2 hours at the same temperature. Filtered the precipitated solid, washed with water and dried for 24 hours at 60-65° C. to get the title compound.

Yield: 122 gms; Purity by HPLC: 99.88%.

Figure 4:
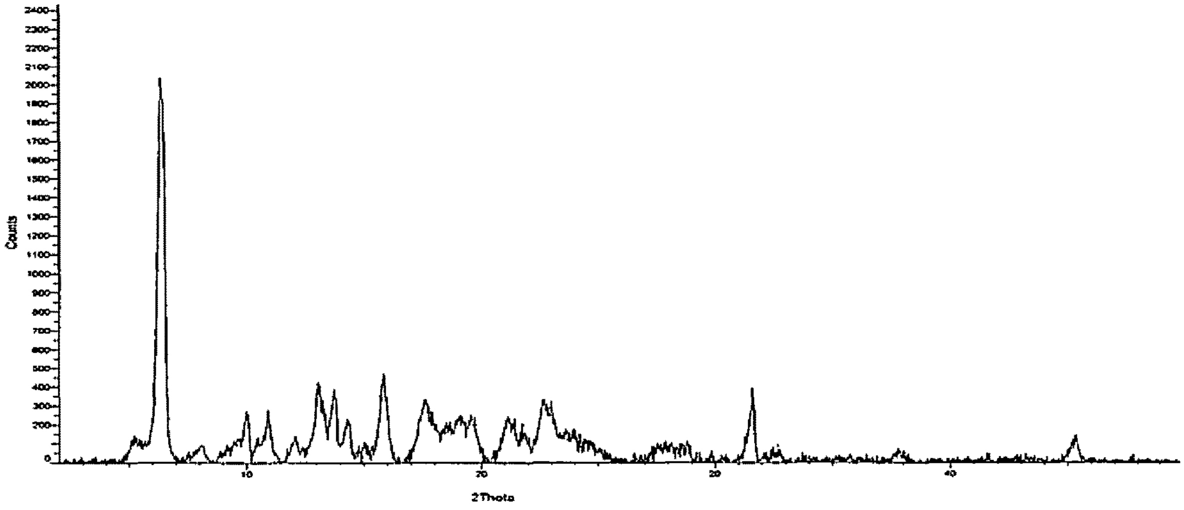
FIG. 4: Illustrates the PXRD pattern of crystalline form-S3 of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxybenzoic acid 2-butanol solvate compound of formula-1.

The P-XRD pattern of the obtained compound was depicted in FIG. 4.

Example-8

Preparation of Amorphous Form of Eluxadoline

A mixture of 5-(((S)-2-amino-3-(4-carbamoyl-2,6-dimethylphenyl)-N—((S)-1-(4-phenyl-1H-imidazol-2-yl)ethyl) propanamido)methyl)-2-methoxy benzoic acid butanol solvate (100 gms), acetonitrile (150 ml) and water (150 ml) was stirred for 10 minutes at 25-30° C. Heated the reaction mixture to 40-45° C. and stirred for 15 minutes at the same temperature. Filtered the reaction mixture through hyflow bed and washed with a mixture of acetonitrile and water. The reaction mixture was added to pre-cooled water at 0-5° C. and stirred for 2 hours at the same temperature. Filtered the precipitated solid, washed with chilled water and dried to get the title compound. Yield: 70.0 gms; M.R: 180-186° C.; Purity by HPLC: 99.95%.

Example-9

Preparation of Amorphous Form of Eluxadoline

A mixture of 5-(((S)-2-amino-3-(4-carbamoyl-2,6-dimethylphenyl)-N—((S)-1-(4-phenyl-1H-imidazol-2-yl)ethyl) propanamido)methyl)-2-methoxy benzoic acid 2-butanol solvate (5.0 gms), acetonitrile (5.0 ml) and water (5.0 ml) was stirred for 10 minutes at 25-30° C. The reaction mixture was slowly added to pre-cooled water (50 ml) at 0-5° C. and stirred for 2 hours minutes at the same temperature. Filtered the precipitated solid, washed with water and dried to get the title compound. Yield: 2.9 gms; Purity by HPLC: 99.92%.

Example-10

Preparation of Amorphous Form of Eluxadoline

A mixture of 5-(((S)-2-amino-3-(4-carbamoyl-2,6-dimethylphenyl)-N—((S)-1-(4-phenyl-1H-imidazol-2-yl)ethyl) propanamido)methyl)-2-methoxy benzoic acid 2-butanol solvate (2.0 gms), acetonitrile (2 ml) and water (2 ml) was heated to 40-45° C. The reaction mixture was slowly added to pre-cooled acetone (40 ml) at −40° C. and stirred for 2 hours at the same temperature. Filtered the precipitated solid, washed with water and dried to get the title compound. Yield: 1.3 gms.

Example-11

Preparation of Amorphous Form of Eluxadoline

A mixture of 5-(((S)-2-amino-3-(4-carbamoyl-2,6-dimethylphenyl)-N—((S)-1-(4-phenyl-1H-imidazol-2-yl)ethyl) propanamido)methyl)-2-methoxy benzoic acid 2-butanol solvate (2 gms), acetonitrile (3 ml) and water (3 ml) was heated to 40-45° C. The reaction mixture was slowly added to pre-cooled acetonitrile (20 ml) at 0-5° C. and stirred for 60 minutes at the same temperature. Filtered the precipitated solid, washed with water and dried to get the title compound. Yield: 1.23 gms.

Example-12

Preparation of Amorphous Form of Eluxadoline

A mixture of 5-(((S)-2-amino-3-(4-carbamoyl-2,6-dimethylphenyl)-N—((S)-1-(4-phenyl-1H-imidazol-2-yl)ethyl) propanamido)methyl)-2-methoxy benzoic acid 2-butanol solvate (5.0 gms), acetonitrile (3.5 ml), methanol (3.5 ml) and water (3.5 ml) was stirred for 10 minutes at 25-30° C. The reaction mixture was slowly added to pre-cooled water (3.5 ml) at 0-5° C. and stirred for 2 hours minutes at the same temperature. Filtered the precipitated solid, washed with water and dried to get the title compound. Yield: 3.1 gms.

Example-13

Preparation of Crystalline Form-N of Eluxadoline

Methanol (250 ml) was added to 5-(((S)-2-amino-3-(4-carbamoyl-2,6-dimethyl phenyl)-N—((S)-1-(4-phenyl-1H-imidazol-2-yl)ethyl)propanamido)methyl)-2-methoxy benzoic acid 2-butanol solvate (50 gms) at 25-30° C. and stirred for 15 minutes at the same temperature. Heated the reaction mixture to 40-45° C. and stirred for 1 hour at the same temperature. Cooled the reaction mixture to 25-30° C. and stirred for 30 minutes at the same temperature. Filtered the solid, washed with methanol and dried to get the title compound.

Yield: 45.0 gms; The P-XRD pattern of the obtained compound was depicted in FIG. 5.

Example-14

Preparation of Crystalline Form-M1 of Eluxadoline

Propylene glycol (2.0 ml) was added to 5-(((S)-2-amino-3-(4-carbamoyl-2,6-dimethyl phenyl)-N—((S)-1-(4-phenyl-1H-imidazol-2-yl)ethyl)propanamido)methyl)-2-methoxy benzoic acid 2-butanol solvate (0.5 gms) at 25-30° C. and stirred for 15 minutes at the same temperature. Heated the reaction mixture to 60-65° C. and stirred for 30 minutes at the same temperature. Cooled the reaction mixture to 25-30° C. and stirred for 30 minutes at the same temperature. Filtered the solid, washed with methanol and dried to get the title compound.

Yield: 0.46 gms; The P-XRD pattern of the obtained compound was depicted in FIG. 6.

Example-15

Preparation of Crystalline Form-M2 of Eluxadoline

Anisole (7.0 ml) was added to 5-(((S)-2-amino-3-(4-carbamoyl-2,6-dimethyl phenyl)-N—((S)-1-(4-phenyl-1H-imidazol-2-yl)ethyl)propanamido)methyl)-2-methoxy benzoic acid 2-butanol solvate (1.0 gms) at 25-30° C. and stirred for 15 minutes at the same temperature. Heated the reaction mixture to 40-45° C. and stirred for 30 minutes at the same temperature. Cooled the reaction mixture to 25-30° C. and stirred for 30 minutes at the same temperature. Filtered the solid, washed with methanol and dried to get the title compound.

Yield: 0.6 gms; The P-XRD pattern of the obtained compound was depicted in FIG. 7.

Example-16

Preparation of Crystalline Form-N3 of Eluxadoline

Benzyl alcohol (2.0 ml) was added to 5-(((S)-2-amino-3-(4-carbamoyl-2,6-dimethylphenyl)-N—((S)-1-(4-phenyl-1H-imidazol-2-yl)ethyl)propanamido)methyl)-2-methoxy benzoic acid 2-butanol solvate (0.5 gms) at 25-30° C. Heated the reaction mixture to 60-65° C. and stirred for 30 minutes at the same temperature. Cooled the reaction mixture to 25-30° C. and stirred for 30 minutes at the same temperature. Filtered the reaction mixture. 2-butanol (1.5 ml) was added to the obtained filtrate at 25-30° C. and stirred form 30 minutes at the same temperature. Filtered the precipitated solid, washed with 2-butanol and dried to get the title compound. Yield: 0.30 gms.

The P-XRD pattern of the obtained compound was depicted in FIG. 12.

Example-17

Preparation of (S)-methyl-2-methoxy-5-(((1-(4-phenyl-1H-imidazol-2-yl)ethyl)amino)methyl)benzoate: (Formula-2)

(S)-1-(4-phenyl-1H-imidazol-2-yl)ethanamine (48.2 gms) was added to a mixture of methyl-5-formyl-2-methoxybenzoate (50 gms) and methanol (300 ml) at 25-30° C. and stirred for 2 hours at the same temperature. Cooled the reaction mixture to 0-5° C. Sodium borohydride (12.6 gms) was added to the reaction mixture at 0-5° C. and stirred for 4 hours at the same temperature. Water (250 ml) was slowly added to the reaction mixture at 0-5° C. pH of reaction mixture was adjusted to 2.0 using aqueous hydrochloric acid solution (75 ml) at 0-5° C. Ethyl acetate (250 ml) was added to the reaction mixture at 0-5° C. Basified the reaction mixture using 10% sodium hydroxide solution at 0-5° C. Raised the reaction temperature to 25-30° C. and stirred for 30 minutes at the same temperature. Both the organic and aqueous layers were separated and aqueous layer was extracted with ethyl acetate. Combine the organic layer and washed with aqueous sodium chloride solution. Distilled off the solvent completely from the organic layer under reduced pressure. Isopropanol (250 ml) was added to the obtained residue at 25-30° C. and stirred for 10 minutes at the same temperature. Distilled off the solvent completely from the reaction mixture under reduced pressure to get the title compound. Yield: 93.2 gms; Purity by HPLC: 91.16%.

Example-18

Preparation of maleate salt of (S)-methyl-2-methoxy-5-(((1-(4-phenyl-1H-imidazol-2-yl)ethyl)amino)methyl)benzoate: (Formula-2a)

Isopropanol (400 ml) was added to (S)-methyl-2-methoxy-5-(((1-(4-phenyl-1H-imidazol-2-yl)ethyl)amino)methyl)benzoate (93.2 gms) at 25-30° C. and stirred for 10 minutes at the same temperature. Maleic acid (29.8 gms) was added to the reaction mixture at 25-30° C. and stirred for 2 hours at the same temperature. Filtered the precipitated solid, washed with isopropanol and dried to get the title compound. Yield: 105 gms; M.R: 154-158° C.; Purity by HPLC: 97.49%; The P-XRD pattern of the obtained compound is depicted in FIG. 8.

Example-19

Preparation of oxalate salt of (S)-methyl-2-methoxy-5-(((1-(4-phenyl-1H-imidazol-2-yl)ethyl)amino)methyl)benzoate: (Formula-2b)

Isopropanol (400 ml) was added to (S)-methyl-2-methoxy-5-(((1-(4-phenyl-1H-imidazol-2-yl) ethyl)amino) methyl)benzoate (93.2 gms) at 25-30° C. and stirred for 10 minutes at the same temperature. Oxalic acid (23.2 gms) was added to the reaction mixture at 25-30° C. and stirred for 2 hours at the same temperature. Filtered the precipitated solid, washed with isopropanol and dried to get the title compound. Yield: 106 gms; M.R: 160-163° C. Purity by HPLC: 98.32%; The P-XRD pattern of the obtained compound is depicted in FIG. 9.

Example-20

Preparation of methyl-5-(((S)-2-((tertiarybutoxycarbonyl)amino)-3-(4-carbamoyl-2,6-dimethylphenyl)-N—((S)-1-(4-phenyl-1H-imidazol-2-yl)ethyl)propan amido)methyl)-2-methoxybenzoate Acetonitrile (125 ml) was added to (S)-2-((tertiarybutoxycarbonyl)amino)-3-(4-carbamoyl-2,6-dimethylphenyl)propanoic acid (25 gms) at 25-30° C. and stirred for 10 minutes at the same temperature. Cooled the reaction mixture to 10-15° C. Hydroxybenzotriazole (5.0 gms), N-(3-Dimethylaminopropyl)-N'-ethyl carbodiimide hydrochloride (14.2 gms) and (S)-methyl-2-methoxy-5-(((1-(4-phenyl-1H-imidazol-2-yl)ethyl)amino)methyl)benzoate maleate (35.7 gms) were added to the reaction mixture at 10-15° C. and stirred for 5 minutes at the same temperature. Diisopropylethylamine (19.2 gms) was slowly added to the reaction mixture at 10-15° C. Raised the temperature of the reaction mixture to 25-30° C. and stirred for 90 minutes at the same temperature. N-(3-Dimethylaminopropyl)-N'-ethyl carbodiimide hydrochloride (7.1 gms) was added to the reaction mixture at 25-30° C. and stirred for 1 hour at the same temperature. Water and ethyl acetate were added to the reaction mixture at 25-30° C. and stirred for 20 minutes at the same temperature. Both the organic and aqueous layers were separated and aqueous layer was extracted with ethyl acetate at 25-30° C. Both the organic layers were washed twice with aqueous sodium carbonate solution followed by aqueous hydrochloric acid solution at 25-30° C. Organic layer was washed with aqueous sodium chloride solution at 25-30° C. and distilled off the solvent completely from the organic layer under reduced pressure. Cyclohexane (118.75 ml) was added to the obtained compound at 25-30° C. and stirred for 1 hour at the same temperature. Filtered the precipitated solid, washed with cyclohexane and dried to get the title compound.

Yield: 45 gms; M.R: 125-130° C.; Purity by HPLC: 98.9 %.

Example-21

Preparation of Amorphous 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxy benzoic acid in combination with PVP K-30

Methanol (30 ml) was added to a mixture of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxy benzoic acid (1.0 gms) and polyvinyl pyrrolidone K-30 (1.0 gms) at 25-30° C. and stirred for 30 minutes at the same temperature. Filtered the reaction mixture through hyflow bed. Distilled off the solvent completely from the obtained filtrate under reduced pressure to get the title compound. Yield: 1.5 gms.

The P-XRD pattern of the obtained compound was depicted in FIG. 16.

Example-22

Preparation of Amorphous 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxy benzoic acid in combination with HPC Methanol (30 ml) was added to a mixture of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxy benzoic acid (1.0 gms) and hydroxypropyl cellulose (1.0 gms) at 25-30° C. and stirred for 30 minutes at the same temperature. Filtered the reaction mixture through hyflow bed. Distilled off the solvent completely from the obtained filtrate under reduced pressure to get the title compound. Yield: 1.2 gms.

The P-XRD pattern of the obtained compound was depicted in FIG. 13.

Example-23

Preparation of Amorphous 5-[[[(2S)-2-amino-3-[4-(aminocarbonyl)-2,6-dimethylphenyl]-1-oxopropyl]((1S)-1-(4-phenyl-1H-imidazol-2-yl)ethyl]amino)methyl]-2-methoxy benzoic acid in combination with HPMC Methanol (30 ml) was added to a mixture of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxy benzoic acid (1.0 gms) and hydroxypropyl methylcellulose (1.0 gms) at 25-30° C. and stirred for 30 minutes at the same temperature. Filtered the reaction mixture through hyflow bed. Distilled off the solvent completely from the obtained filtrate under reduced pressure to get the title compound. Yield: 1.5 gms.

The P-XRD pattern of the obtained compound was depicted in FIG. 15.

Example-24

Preparation of Amorphous 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxy benzoic acid in combination with HPMC AS Methanol (30 ml) was added to a mixture of 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxy benzoic acid (1.0 gms) and hydroxypropyl methylcellulose acetate succinate (1.0 gms) at 25-30° C. and stirred for 30 minutes at the same temperature. Filtered the reaction mixture through hyflow bed.

Distilled off the solvent completely from the obtained filtrate under reduced pressure to get the title compound. Yield: 1.0 gms.

The P-XRD pattern of the obtained compound was depicted in FIG. 14.

Example-25

Preparation of Amorphous Form of Eluxadoline

Methanol (30 ml) was added to 5-[[[(2S)-2-amino-3-[4-(aminocarbonyl)-2,6-dimethyl phenyl]-1-oxopropyl][(1S)-1-(4-phenyl-1H-imidazol-2-yl)ethyl]amino]methyl]-2-methoxy benzoic acid (1.0 gms) at 25-30° C. and stirred for 30 minutes. Filtered the reaction mixture through hyflow bed. Distilled off the solvent completely from the obtained filtrate under reduced pressure to get the title compound. Yield: 0.7 gms.

Example-26

Preparation of Amorphous Form of Eluxadoline:

Methanol (200 ml) was added to 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid (5 gms) at 25-30° C. and stirred for 20 minutes at the same temperature. Filtered the reaction mixture through hyflow bed. The obtained filtrate was spray dried at below mentioned parameters to obtain the title compound.

Operation Parameters:

Labultima Instrument.

Aspirator: 70%

Feed Rate: 10 ml/min

Inlet temperature: 55° C. to 60° C.

Gas flow $N_2$: 2 $kg/cm^2$

Yield: 2.0 gms; The P-XRD pattern of the obtained compound was depicted in FIG. 17.

Example-27

Preparation of Crystalline Form-N1 of Eluxadoline

A mixture of isopropanol (60 ml) and 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxy benzoic acid (3.0 gms) were heated to 60-65° C. and stirred for 6 hours at the same temperature. Cooled the reaction mixture to 25-30° C. and stirred for 1 hour at the same temperature. Filtered the solid, washed with isopropanol and dried to get the title compound.

Yield: 2.8 gms; The P-XRD pattern of the obtained compound was depicted in FIG. 10.

Example-28

Preparation of Crystalline Form-N2 of Eluxadoline

Ethyl formate (5.0 ml) was added to 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxy benzoic acid (0.5 gms) at 25-30° C. Heated the reaction mixture to 60-65° C. Ethyl acetate (5.0 ml) added to the reaction mixture at 60-65° C. and stirred for 10 minutes. Methyl tert-butyl ether (5.0 ml) was added to the reaction mixture at 60-65° C. and stirred for 6 hours at the same temperature. Cooled the reaction mixture to 25-30° C. and stirred for 15 minutes at the same temperature. Filtered the precipitated solid and dried to get the title compound. Yield: 0.3 gms. The P-XRD pattern of the obtained compound was depicted in FIG. 11.

Example-29

Preparation of Crystalline Form-N3 of Eluxadoline

A mixture of methyl isobutyl ketone (60 ml) and 5-[[[(2S)-2-amino-3-[4-(amino carbonyl)-2,6-dimethylphenyl]-1-oxopropyl][(1S)-1-(4-phenyl-1H-imidazol-2-yl)ethyl] amino]methyl]-2-methoxybenzoic acid (3.0 gms) were heated to 60-65° C. and stirred for 6 hours at the same temperature. Cooled the reaction mixture to 25-30° C. and stirred for 1 hour at the same temperature. Filtered the solid and dried to get the title compound.

Yield: 2.6 gms; The P-XRD pattern of the obtained compound was depicted in FIG. 12.

Example-30

Preparation of Amorphous Form of Eluxadoline

5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid hydrochloride compound of formula-1a (2.0 gms) was added to water (10.0 ml) and stirred for 10 minutes at the same temperature. Aqueous sodium hydroxide solution was slowly added to the reaction mixture at 25-30° C. and stirred for 30 minutes at the same temperature. Filtered the precipitated solid, washed with water and dried to get the title compound. Yield: 1.2 gms; Purity by HPLC: 99.97%;

Particle Size Distribution (PSD): D(0.1) is 3.1 μm; D(0.5) is 41.6 μm; D(0.9) is 479.9 μm; D[4.3] is 156.3 μm; The P-XRD pattern of the obtained compound is depicted in FIG. 17.

Example-31

Preparation of Amorphous of Eluxadoline

Water (2.0 ml) was added to 5-((4S)-4-(tert-butoxycarbonylamino)-5-(4-carbamoyl-2,6-dimethylphenyl)-3-oxo-2-((R)-1-(4-phenyl-1H-imidazol-2-yl)ethyl)pentyl)-2-methoxy benzoic acid (2.0 gms) at 25-30° C. Aqueous hydrochloric acid solution (4.0 ml) was slowly added to the reaction mixture at 15-20° C. Raised the temperature of the reaction mixture to 25-30° C. and stirred for 30 minutes at the same temperature. Basifying the reaction mixture using aqueous sodium hydroxide solution at 25-30° C. and stirred for 30 minutes at the same temperature. Filtered the precipitated solid, washed with water and dried to get the title compound. Yield: 0.9 gms; Purity by HPLC: 99.98%.

Particle Size Distribution (PSD): D(0.1) is 7.6 μm; D(0.5) is 76.0 μm; D(0.9) is 330.0 μm; D[4.3] is 127.2 μm; The P-XRD pattern of the obtained compound is depicted in FIG. 17.

Reference Example 1

Preparation of 5-[[[(2S)-2-amino-3-[4-(aminocarbonyl)-2,6-dimethylphenyl]-1-oxopropyl][(1S)-1-(4-phenyl-1H-imidazol-2yl)ethyl]amino]methyl]-2-methoxy benzoic acid (Example-1 of U.S. Pat. No. 7,994,206 B2)

A 1 L three-necked round-bottomed flask equipped with a mechanical stirrer, addition funnel and a thermocouple was charged without agitation. 34.2 g of 5-({[2-tert-butoxy carbonylamino-3-(4-carbamoyl-2,6-dimethyl -phenyl)-propionyl]-[1-(4-phenyl-1H-imidazol-2-yl)-ethyl]-amino}-methyl)-2-methoxybenzoic acid, 340 ml of acetone, and 17 ml of 204 m molar concentrated HCl were combined in the flask. The stirring was started and the resulting slurry formed a clear solution. This solution was heated to 45° C. under vigorous stirring and aged at this temperature for a period of 2 hours. After the completion, the reaction mass was cooled to ambient temperature and the supernatant was removed by suction. The vessel along with the residue was rinsed with 20 ml of acetone and then removed as previously. 170 ml of water was added and the reaction mass was aged under stirring until a homogenous solution resulted. This solution was then added over a period of 30 minutes to a solution of 90 ml of 1N NaOH and water. The pH was adjusted to 6.5-7.0 accordingly. The resulting slurry was aged for about 2 hours at ambient temperature, cooled to 10-15° C., aged at that temperature for about 1 hour, and then filtered. The solid was washed with 10 ml water, air-dried for a period of 4 to 5 hours, and then placed in a vacuum oven at 50-55° C. until the water content was less than 3%.

Figure 18:
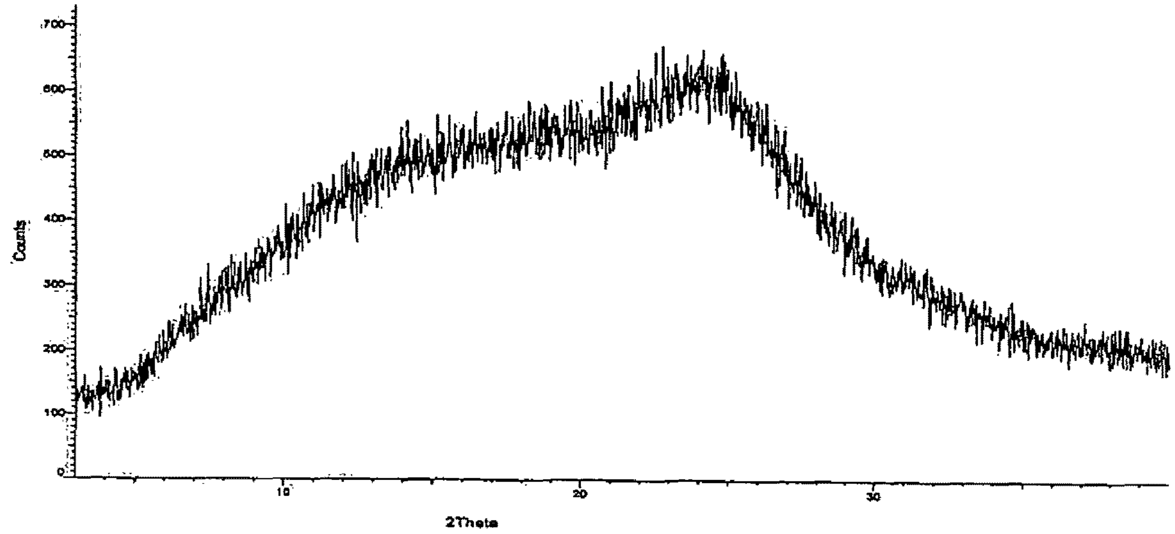
FIG. 18: Illustrates the PXRD pattern of amorphous of 5-[[[(2S)-2-amino-3-[4-(amino carbonyl)-2,6-dimethylphenyl]-1-oxopropyl][(1S)-1-(4-phenyl-1H-imidazol-2-yl) ethyl]amino]methyl]-2-methoxybenzoic acid obtained according to reference example-1.

The P-XRD of the obtained compound was depicted in FIG. 18.

We claim:

1. A process for the preparation of amorphous form of Eluxadoline, comprising:

a) providing a solution of Eluxadoline 2-butanol solvate in a solvent, and b) isolating amorphous form of Eluxadoline.

2. The process according to claim 1, wherein the obtained amorphous form of Eluxadoline is characterized by its powder x-ray diffraction pattern as illustrated in FIG. 17.

3. The process according to claim 1, wherein providing a solution of Eluxdoline 2-butanol solvate in step-a) is carried out by dissolving Eluxadoline 2-butanol solvate in a solvent at a temperature ranging from 25° C. to reflux temperature of the solvent used therein.

4. The process according to claim 1, wherein the solvent used in step-a) is selected from alcohol solvents, nitrile solvents, hydrocarbon solvents, ketone solvents, ester solvents, water or mixture thereof.

5. The process according to claim 1, wherein isolating the amorphous form of Eluxadoline in step-b) is by cooling, decantation, filtration by gravity or suction, centrifugation, adding to solvent to make slurry followed by filtration.

* * * * *